(12) United States Patent
Tu et al.

(10) Patent No.: US 9,561,131 B2
(45) Date of Patent: *Feb. 7, 2017

(54) IMPLANT DELIVERY SYSTEM AND METHODS THEREOF FOR TREATING OCULAR DISORDERS

(75) Inventors: Hosheng Tu, Newport Coast, CA (US); David Steven Haffner, Mission Viejo, CA (US); Gregory T. Smedley, Aliso Viejo, CA (US); Barbara A. Niksch, Laguna Nigel, CA (US); Morteza Gharib, San Marino, CA (US); Thomas W. Burns, Dana Point, CA (US); Richard Lindstrom, Wayzata, MN (US)

(73) Assignee: Glaukos Corporation, San Clemente, CA (US)

( * ) Notice: Subject to any disclaimer, the term of this patent is extended or adjusted under 35 U.S.C. 154(b) by 2069 days.

This patent is subject to a terminal disclaimer.

(21) Appl. No.: 11/455,598

(22) Filed: Jun. 19, 2006

(65) Prior Publication Data

US 2006/0241749 A1  Oct. 26, 2006

Related U.S. Application Data

(63) Continuation of application No. 10/231,342, filed on Aug. 28, 2002, now Pat. No. 7,331,984.

(Continued)

(51) Int. Cl.
*A61F 9/007* (2006.01)
*A61M 27/00* (2006.01)

(52) U.S. Cl.
CPC ......... *A61F 9/00781* (2013.01); *A61M 27/002* (2013.01)

(58) Field of Classification Search
CPC ..................... A61M 27/002; A61F 9/00781
(Continued)

(56) References Cited

U.S. PATENT DOCUMENTS 2,269,963 A   1/1942   Frederick
3,439,675 A   4/1969   Cohen
(Continued)

FOREIGN PATENT DOCUMENTS

AU   200072059 A1   7/2001
CA      2244646 A1   2/1999
(Continued)

OTHER PUBLICATIONS

Phillip C. Jacobi, MD, Thomas S. Dietleln, MD and Gunter K. Krieglstein, *Goniocurettage for Removing Trabecular Meshwork: Clinical Resuls of a new Surgical Technique in Advanced Cronic Open-Angle Glaucoma*, American Journal of Ophthalmology, May 1999, pp. 506-610.

(Continued)

*Primary Examiner* — Katherine M Shi
*Assistant Examiner* — Michael Mendoza
(74) *Attorney, Agent, or Firm* — Knobbe Martens Olson & Bear LLP

(57) ABSTRACT

Surgical methods and related medical devices for treating glaucoma are disclosed. The method comprises trabecular bypass surgery, which involves bypassing diseased trabecular meshwork with the use of a stent implant. The stent implant is inserted into an opening created in the trabecular meshwork by a piercing member that is slidably advanceable through the lumen of the stent implant for supporting the implant insertion. The stent implant is positioned through the trabecular meshwork so that an inlet end of the stent implant is exposed to the anterior chamber of the eye and an outlet end is positioned into fluid collection channels (Continued)

at about an exterior surface of the trabecular meshwork or up to the level of aqueous veins.

18 Claims, 16 Drawing Sheets

Related U.S. Application Data

(60) Provisional application No. 60/315,463, filed on Aug. 28, 2001, provisional application No. 60/363,980, filed on Mar. 14, 2002.

(58) Field of Classification Search
USPC .......................... 606/108; 623/1.11; 604/294
See application file for complete search history.

(56) References Cited

U.S. PATENT DOCUMENTS

| | | |
|---|---|---|
| 3,788,327 A | 1/1974 | Donowitz et al. |
| 3,948,271 A | 4/1976 | Akiyama |
| 3,948,871 A | 4/1976 | Butterfield et al. |
| 3,976,077 A | 8/1976 | Kerfoot, Jr. |
| 4,037,604 A | 7/1977 | Newkirk |
| 4,113,088 A | 9/1978 | Binkhorst |
| 4,168,697 A | 9/1979 | Cantekin |
| 4,175,563 A | 11/1979 | Arenberg et al. |
| 4,299,227 A | 11/1981 | Lincoff |
| 4,366,582 A | 1/1983 | Faulkner |
| 4,402,681 A | 9/1983 | Haas et al. |
| 4,428,746 A | 1/1984 | Mendez |
| 4,449,529 A | 5/1984 | Burns et al. |
| 4,501,274 A | 2/1985 | Skjaerpe |
| 4,521,210 A | 6/1985 | Wong |
| 4,554,918 A | 11/1985 | White |
| 4,560,383 A | 12/1985 | Leiske |
| 4,578,058 A | 3/1986 | Grandon |
| 4,583,224 A | 4/1986 | Ishii et al. |
| 4,604,087 A | 8/1986 | Joseph |
| 4,632,842 A | 12/1986 | Karwoski et al. |
| 4,634,418 A | 1/1987 | Binder |
| 4,642,090 A | 2/1987 | Ultrata |
| 4,718,907 A | 1/1988 | Karwoski et al. |
| 4,722,724 A | 2/1988 | Schocket |
| 4,733,665 A | 3/1988 | Palmaz |
| 4,750,901 A | 6/1988 | Molteno |
| 4,787,885 A | 11/1988 | Binder |
| 4,800,870 A | 1/1989 | Reid, Jr. |
| 4,800,890 A | 1/1989 | Cramer |
| 4,804,382 A | 2/1989 | Turina et al. |
| 4,820,626 A | 4/1989 | Williams et al. |
| 4,846,172 A | 7/1989 | Berlin |
| 4,846,793 A | 7/1989 | Leonard et al. |
| 4,853,224 A | 8/1989 | Wong |
| 4,863,457 A | 9/1989 | Lee |
| 4,867,173 A | 9/1989 | Leoni |
| 4,870,953 A | 10/1989 | DonMichael et al. |
| 4,883,864 A | 11/1989 | Scholz |
| 4,886,488 A | 12/1989 | White |
| 4,900,300 A | 2/1990 | Lee |
| 4,905,667 A | 3/1990 | Foerster et al. |
| 4,936,825 A | 6/1990 | Ungerleider |
| 4,946,436 A | 8/1990 | Smith |
| 4,968,296 A | 11/1990 | Ritch et al. |
| 4,991,602 A | 2/1991 | Amplatz et al. |
| 4,997,652 A | 3/1991 | Wong |
| 5,005,577 A | 4/1991 | Frenekl |
| 5,041,081 A | 8/1991 | Odrich |
| 5,053,040 A | 10/1991 | Goldsmith, III |
| 5,053,044 A | 10/1991 | Mueller et al. |
| 5,073,163 A | 12/1991 | Lippman |
| 5,092,837 A | 3/1992 | Ritch et al. |
| 5,095,887 A | 3/1992 | Leon et al. |
| 5,127,901 A | 7/1992 | Odrich |
| 5,129,895 A | 7/1992 | Vassiliadis et al. |
| 5,164,188 A | 11/1992 | Wong |
| 5,169,386 A | 12/1992 | Becker et al. |
| 5,171,213 A | 12/1992 | Price, Jr. |
| 5,178,604 A | 1/1993 | Baerveldt et al. |
| 5,180,362 A | 1/1993 | Worst |
| 5,207,685 A | 5/1993 | Cinberg et al. |
| 5,221,255 A | 6/1993 | Mahurkar et al. |
| 5,246,451 A | 9/1993 | Trescony et al. |
| 5,284,476 A | 2/1994 | Koch |
| 5,290,295 A | 3/1994 | Querals et al. |
| 5,300,020 A | 4/1994 | L'Esperance, Jr. |
| 5,318,513 A | 6/1994 | Leib et al. |
| 5,324,306 A | 6/1994 | Makower et al. |
| 5,334,137 A | 8/1994 | Freeman |
| 5,338,291 A | 8/1994 | Speckman et al. |
| 5,342,370 A | 8/1994 | Simon et al. |
| 5,346,464 A | 9/1994 | Camras |
| 5,360,399 A | 11/1994 | Stegmann |
| 5,370,607 A | 12/1994 | Memmen |
| 5,370,641 A | 12/1994 | O'Donnell, Jr. |
| 5,372,577 A | 12/1994 | Ungerleider |
| 5,397,300 A | 3/1995 | Baerveldt et al. |
| 5,415,666 A | 5/1995 | Gourlay et al. |
| 5,433,701 A | 7/1995 | Rubinstein |
| 5,443,505 A | 8/1995 | Wong et al. |
| 5,445,637 A | 8/1995 | Bretton |
| 5,454,796 A | 10/1995 | Krupin |
| 5,462,558 A | 10/1995 | Kolesa et al. |
| 5,472,440 A | 12/1995 | Beckman |
| 5,476,445 A | 12/1995 | Baerveldt et al. |
| 5,486,165 A | 1/1996 | Stegmann |
| 5,502,052 A | 3/1996 | DeSantis |
| 5,516,522 A | 5/1996 | Peyman et al. |
| 5,520,631 A | 5/1996 | Nordquist et al. |
| 5,547,993 A | 8/1996 | Miki |
| 5,556,400 A | 9/1996 | Tunis |
| 5,557,453 A | 9/1996 | Schalz et al. |
| 5,558,629 A | 9/1996 | Baerveldt et al. |
| 5,558,630 A | 9/1996 | Fisher |
| 5,558,637 A | 9/1996 | Allonen et al. |
| 5,562,641 A | 10/1996 | Flomenblit et al. |
| RE35,390 E | 12/1996 | Smith |
| 5,601,094 A | 2/1997 | Reiss |
| 5,601,549 A | 2/1997 | Miyagi |
| 5,626,558 A | 5/1997 | Suson |
| 5,626,559 A | 5/1997 | Solomon |
| 5,626,588 A | 5/1997 | Sauer et al. |
| 5,639,278 A | 6/1997 | Dereume et al. |
| 5,643,321 A | 7/1997 | McDevitt |
| 5,651,782 A | 7/1997 | Simon et al. |
| 5,651,783 A | 7/1997 | Reynard |
| 5,652,236 A | 7/1997 | Krauss |
| 5,653,724 A | 8/1997 | Imonti |
| 5,663,205 A | 9/1997 | Ogawa et al. |
| 5,665,114 A | 9/1997 | Weadock et al. |
| 5,669,501 A | 9/1997 | Hissong et al. |
| 5,670,161 A | 9/1997 | Healy et al. |
| 5,676,679 A | 10/1997 | Simon et al. |
| 5,681,275 A | 10/1997 | Ahmed |
| 5,681,323 A | 10/1997 | Arick |
| 5,695,479 A | 12/1997 | Jagpal |
| 5,702,414 A | 12/1997 | Richter et al. |
| 5,702,419 A | 12/1997 | Berry et al. |
| 5,704,907 A | 1/1998 | Nordquist et al. |
| 5,713,844 A | 2/1998 | Peyman |
| 5,723,005 A | 3/1998 | Herrick |
| 5,725,493 A * | 3/1998 | Avery et al. ...................... 604/9 |
| 5,725,546 A | 3/1998 | Samson |
| 5,733,256 A | 3/1998 | Costin |
| 5,741,292 A | 4/1998 | Mendius |
| 5,741,333 A | 4/1998 | Frid |
| 5,743,868 A | 4/1998 | Brown et al. |
| 5,752,928 A | 5/1998 | de Roulhac et al. |
| 5,762,625 A | 6/1998 | Igaki |
| 5,766,242 A | 6/1998 | Wong et al. |
| 5,766,243 A | 6/1998 | Christensen et al. |
| 5,767,079 A | 6/1998 | Glaser et al. |
| 5,785,674 A | 7/1998 | Mateen |
| 5,792,099 A | 8/1998 | DeCamp et al. |

(56) References Cited

U.S. PATENT DOCUMENTS

| | | |
|---|---|---|
| 5,807,244 A | 9/1998 | Barot |
| 5,807,302 A | 9/1998 | Wandel |
| 5,810,870 A | 9/1998 | Myers et al. |
| 5,814,620 A | 9/1998 | Robinson et al. |
| 5,817,100 A | 10/1998 | Igaki |
| 5,824,072 A | 10/1998 | Wong |
| 5,830,139 A | 11/1998 | Abreu |
| 5,830,171 A | 11/1998 | Wallace |
| 5,833,694 A | 11/1998 | Poncet |
| 5,836,939 A | 11/1998 | Negus et al. |
| 5,840,041 A | 11/1998 | Petter et al. |
| 5,865,831 A | 2/1999 | Cozean et al. |
| 5,868,697 A | 2/1999 | Ritcher et al. |
| 5,869,468 A | 2/1999 | Freeman |
| 5,879,319 A | 3/1999 | Pynson et al. |
| 5,882,327 A | 3/1999 | Jacob |
| 5,886,822 A | 3/1999 | Spitzer |
| 5,891,084 A | 4/1999 | Lee |
| 5,893,837 A | 4/1999 | Eagles et al. |
| 5,908,449 A | 6/1999 | Bruchman et al. |
| 5,925,342 A | 7/1999 | Adorante et al. |
| 5,932,299 A | 8/1999 | Katoot |
| 5,941,250 A | 8/1999 | Aramant et al. |
| 5,952,378 A | 9/1999 | Stjernschantz et al. |
| 5,968,058 A | 10/1999 | Richter et al. |
| 5,980,928 A | 11/1999 | Terry |
| 5,981,598 A | 11/1999 | Tatton |
| 5,984,913 A | 11/1999 | Kritzinger et al. |
| 6,004,302 A | 12/1999 | Brierley |
| 6,007,510 A | 12/1999 | Nigam |
| 6,007,511 A | 12/1999 | Prywes |
| 6,030,416 A | 2/2000 | Huo et al. |
| 6,033,434 A | 3/2000 | Borghi |
| 6,036,678 A | 3/2000 | Giungo |
| 6,036,682 A | 3/2000 | Lange et al. |
| 6,045,557 A | 4/2000 | White et al. |
| 6,050,970 A | 4/2000 | Baerveldt |
| 6,050,999 A | 4/2000 | Paraschac et al. |
| 6,059,772 A | 5/2000 | Hsia et al. |
| 6,059,812 A | 5/2000 | Clerc et al. |
| 6,060,463 A | 5/2000 | Freeman |
| 6,063,116 A | 5/2000 | Kelleher |
| 6,063,396 A | 5/2000 | Kelleher |
| 6,071,286 A | 6/2000 | Mawad |
| 6,077,299 A | 6/2000 | Adelberg et al. |
| 6,102,045 A | 8/2000 | Nordquist et al. |
| 6,110,912 A | 8/2000 | Kaufman et al. |
| 6,123,668 A | 9/2000 | Abreu |
| 6,135,977 A | 10/2000 | Drasler et al. |
| 6,142,990 A | 11/2000 | Burk |
| 6,146,387 A | 11/2000 | Trott et al. |
| 6,159,458 A | 12/2000 | Bowman et al. |
| 6,165,210 A | 12/2000 | Lau et al. |
| 6,168,575 B1 | 1/2001 | Soltanpour |
| 6,174,305 B1 | 1/2001 | Mikus et al. |
| 6,177,427 B1 | 1/2001 | Clark et al. |
| 6,184,250 B1 | 2/2001 | Klimko et al. |
| 6,187,016 B1 | 2/2001 | Hedges et al. |
| 6,193,656 B1 | 2/2001 | Jeffries et al. |
| 6,194,415 B1 | 2/2001 | Wheeler et al. |
| 6,197,056 B1 | 3/2001 | Schachar |
| 6,201,001 B1 | 3/2001 | Wang et al. |
| 6,203,513 B1 | 3/2001 | Yaron et al. |
| 6,217,895 B1 | 4/2001 | Guo et al. |
| 6,221,078 B1 | 4/2001 | Bylsma |
| 6,224,570 B1 | 5/2001 | Le et al. |
| 6,228,873 B1 | 5/2001 | Brandt et al. |
| 6,231,597 B1 | 5/2001 | Deem et al. |
| 6,231,853 B1 | 5/2001 | Hillman et al. |
| 6,241,721 B1 | 6/2001 | Cozean et al. |
| 6,251,090 B1 | 6/2001 | Avery et al. |
| 6,254,612 B1 | 7/2001 | Hieshima |
| 6,261,256 B1 | 7/2001 | Ahmed |
| 6,264,668 B1 | 7/2001 | Prywes |
| 6,266,182 B1 | 7/2001 | Morita |
| 6,268,398 B1 | 7/2001 | Ghosh et al. |
| 6,274,138 B1 | 8/2001 | Bandman et al. |
| 6,287,256 B1 | 9/2001 | Park et al. |
| 6,287,313 B1 | 9/2001 | Sasso |
| 6,299,603 B1 | 10/2001 | Hecker et al. |
| 6,299,895 B1 | 10/2001 | Hammang et al. |
| 6,331,313 B1 | 12/2001 | Wong et al. |
| 6,342,058 B1 | 1/2002 | Portney |
| 6,348,042 B1 | 2/2002 | Warren, Jr. |
| 6,355,033 B1 | 3/2002 | Moorman et al. |
| 6,361,519 B1 | 3/2002 | Knudson et al. |
| 6,375,642 B1 | 4/2002 | Grieshaber et al. |
| 6,402,734 B1 | 6/2002 | Weiss |
| 6,405,732 B1 | 6/2002 | Edwards et al. |
| 6,413,540 B1 | 7/2002 | Yaacobi |
| 6,416,777 B1 | 7/2002 | Yaacobi |
| 6,428,501 B1 | 8/2002 | Reynard |
| 6,428,566 B1 * | 8/2002 | Holt ............................ 623/1.11 |
| 6,436,427 B1 | 8/2002 | Hammang et al. |
| 6,450,937 B1 | 9/2002 | Mercereau et al. |
| 6,450,984 B1 | 9/2002 | Lynch et al. |
| 6,454,787 B1 | 9/2002 | Maddalo et al. |
| 6,464,724 B1 | 10/2002 | Lynch et al. |
| 6,471,666 B1 | 10/2002 | Odrich |
| 6,494,857 B1 | 12/2002 | Neuhann |
| 6,524,275 B1 | 2/2003 | Lynch et al. |
| 6,530,896 B1 | 3/2003 | Elliott |
| 6,533,768 B1 | 3/2003 | Hill |
| 6,544,249 B1 | 4/2003 | Yu et al. |
| 6,548,078 B2 | 4/2003 | Guo et al. |
| 6,558,342 B1 | 5/2003 | Yaron et al. |
| 6,561,974 B1 | 5/2003 | Grieshaber et al. |
| 6,579,235 B1 | 6/2003 | Abita et al. |
| 6,582,426 B2 | 6/2003 | Moorman et al. |
| 6,585,680 B2 | 7/2003 | Bugge |
| 6,589,203 B1 | 7/2003 | Mitrev |
| 6,595,945 B2 | 7/2003 | Brown |
| 6,607,542 B1 | 8/2003 | Wild |
| 6,613,343 B2 | 9/2003 | Dillingham et al. |
| 6,620,154 B1 | 9/2003 | Amirkhanian et al. |
| 6,622,473 B2 | 9/2003 | Lynch et al. |
| 6,626,858 B2 | 9/2003 | Lynch et al. |
| 6,629,981 B2 | 10/2003 | Bui et al. |
| 6,638,239 B1 | 10/2003 | Bergheim et al. |
| 6,666,841 B2 | 12/2003 | Gharib et al. |
| 6,676,607 B2 | 1/2004 | De Juan, Jr. et al. |
| 6,699,211 B2 | 3/2004 | Savage |
| 6,699,272 B2 | 3/2004 | Slepian et al. |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,763,833 B1 | 7/2004 | Khera et al. |
| 6,764,439 B2 | 7/2004 | Schaaf et al. |
| 6,767,346 B2 | 7/2004 | Damasco et al. |
| 6,780,164 B2 | 8/2004 | Bergheim et al. |
| 6,780,165 B2 | 8/2004 | Kadziauskas et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,827,738 B2 | 12/2004 | Willis et al. |
| 6,902,577 B2 | 6/2005 | Lipshitz et al. |
| 6,955,656 B2 | 10/2005 | Bergheim et al. |
| 6,981,958 B1 | 1/2006 | Gharib et al. |
| 7,033,603 B2 | 4/2006 | Nelson et al. |
| 7,077,821 B2 | 7/2006 | Durgin |
| 7,094,225 B2 | 8/2006 | Tu et al. |
| 7,135,009 B2 | 11/2006 | Tu et al. |
| 7,135,016 B1 | 11/2006 | Asia et al. |
| 7,217,263 B2 | 5/2007 | Humayun et al. |
| 7,758,624 B2 | 7/2010 | Dorn et al. |
| 8,267,882 B2 | 9/2012 | Euteneuer et al. |
| 8,540,659 B2 | 9/2013 | Berlin |
| 8,679,089 B2 | 3/2014 | Berlin |
| 8,852,266 B2 | 10/2014 | Brooks et al. |
| 9,173,775 B2 | 11/2015 | Haffner et al. |
| 2001/0000527 A1 | 4/2001 | Yaron et al. |
| 2001/0025150 A1 | 9/2001 | de Juan et al. |
| 2002/0013546 A1 | 1/2002 | Grieshaber et al. |

(56) References Cited

U.S. PATENT DOCUMENTS

| | | |
|---|---|---|
| 2002/0013572 A1 | 1/2002 | Berlin |
| 2002/0026200 A1 | 2/2002 | Savage |
| 2002/0072673 A1 | 6/2002 | Yamamoto et al. |
| 2002/0099434 A1 | 7/2002 | Buscemi et al. |
| 2002/0111608 A1 | 8/2002 | Baerveldt et al. |
| 2002/0120284 A1 | 8/2002 | Schachar et al. |
| 2002/0120285 A1 | 8/2002 | Schachar et al. |
| 2002/0133168 A1 | 9/2002 | Smedley et al. |
| 2002/0143284 A1 | 10/2002 | Tu et al. |
| 2002/0165522 A1 | 11/2002 | Holmen |
| 2002/0177856 A1 | 11/2002 | Richter et al. |
| 2002/0188308 A1 | 12/2002 | Tu et al. |
| 2003/0014021 A1 | 1/2003 | Holmen |
| 2003/0014092 A1 | 1/2003 | Neuhann |
| 2003/0055372 A1 | 3/2003 | Lynch et al. |
| 2003/0060752 A1 | 3/2003 | Bergheim et al. |
| 2003/0069637 A1 | 4/2003 | Lynch et al. |
| 2003/0079329 A1 | 5/2003 | Yaron et al. |
| 2003/0088260 A1 | 5/2003 | Smedley et al. |
| 2003/0093084 A1 | 5/2003 | Nissan et al. |
| 2003/0097117 A1 | 5/2003 | Buono |
| 2003/0097151 A1 | 5/2003 | Smedley et al. |
| 2003/0105456 A1 | 6/2003 | Lin |
| 2003/0109907 A1 | 6/2003 | Shadduck |
| 2003/0135149 A1 | 7/2003 | Cullen et al. |
| 2003/0181848 A1 | 9/2003 | Bergheim et al. |
| 2003/0187384 A1 | 10/2003 | Bergheim et al. |
| 2003/0187385 A1 | 10/2003 | Bergheim et al. |
| 2003/0195438 A1 | 10/2003 | Petillo |
| 2003/0208217 A1 | 11/2003 | Dan |
| 2003/0212383 A1 | 11/2003 | Cote et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0050392 A1 | 3/2004 | Tu et al. |
| 2004/0088048 A1 | 5/2004 | Richter et al. |
| 2004/0102729 A1 | 5/2004 | Haffner et al. |
| 2004/0111050 A1 | 6/2004 | Smedley et al. |
| 2004/0127843 A1 | 7/2004 | Tu et al. |
| 2004/0147870 A1 | 7/2004 | Burns et al. |
| 2004/0243227 A1 | 12/2004 | Starksen et al. |
| 2004/0249404 A1 | 12/2004 | Haefliger |
| 2004/0254520 A1 | 12/2004 | Porteous et al. |
| 2005/0038334 A1 | 2/2005 | Lynch et al. |
| 2005/0049578 A1 | 3/2005 | Tu et al. |
| 2005/0075704 A1 | 4/2005 | Tu et al. |
| 2005/0096639 A1 | 5/2005 | Slatkine et al. |
| 2005/0119636 A1 | 6/2005 | Haffner et al. |
| 2005/0119737 A1 | 6/2005 | Bene et al. |
| 2005/0171562 A1 | 8/2005 | Criscuolo et al. |
| 2005/0192527 A1 | 9/2005 | Gharib et al. |
| 2005/0266047 A1 | 12/2005 | Tu et al. |
| 2005/0277864 A1 | 12/2005 | Haffner et al. |
| 2006/0032507 A1 | 2/2006 | Tu |
| 2006/0106370 A1 | 5/2006 | Baerveldt et al. |
| 2006/0116626 A1 | 6/2006 | Smedley et al. |
| 2006/0200113 A1 | 9/2006 | Haffner et al. |
| 2007/0078471 A1 | 4/2007 | Schachar et al. |
| 2007/0123919 A1 | 5/2007 | Schachar et al. |
| 2008/0082078 A1 | 4/2008 | Berlin |
| 2008/0125691 A1 | 5/2008 | Yaron et al. |
| 2008/0140059 A1 | 6/2008 | Schachar et al. |
| 2008/0221501 A1 | 9/2008 | Cote et al. |
| 2008/0228127 A1 | 9/2008 | Burns et al. |
| 2009/0112245 A1 | 4/2009 | Haefliger |
| 2010/0087774 A1 | 4/2010 | Haffner et al. |
| 2010/0185138 A1 | 7/2010 | Yaron et al. |
| 2010/0185205 A1 | 7/2010 | Novakovic et al. |
| 2011/0077626 A1 | 3/2011 | Baerveldt et al. |
| 2011/0092965 A1 | 4/2011 | Slatkine et al. |
| 2012/0203262 A1 | 8/2012 | Connors et al. |

FOREIGN PATENT DOCUMENTS

| | | |
|---|---|---|
| CA | 2643357 | 11/1999 |
| DE | 198 40 047 A1 | 3/2000 |
| EP | 0436232 A1 | 7/1991 |
| EP | 0550791 A | 7/1993 |
| EP | 0 858 788 A1 | 8/1998 |
| EP | 0 898 947 A2 | 3/1999 |
| EP | 1 114 627 A1 | 7/2001 |
| FR | 2 710 269 A1 | 3/1995 |
| FR | 2 721 499 | 12/1995 |
| GB | 2 296 663 A | 7/1996 |
| JP | 11-123205 | 5/1999 |
| RU | 2143250 | 12/1999 |
| WO | WO 89/00869 A1 | 2/1989 |
| WO | WO 91/08784 | 6/1991 |
| WO | WO 91/18568 A1 | 12/1991 |
| WO | WO 92/08406 | 5/1992 |
| WO | WO 92/19294 A1 | 11/1992 |
| WO | WO 94/13234 A1 | 6/1994 |
| WO | WO 94/21205 A1 | 9/1994 |
| WO | WO 95/08310 A1 | 3/1995 |
| WO | WO 98/23237 A1 | 6/1998 |
| WO | WO 98/30181 A1 | 7/1998 |
| WO | WO 98/35639 A1 | 8/1998 |
| WO | WO 98/37831 | 9/1998 |
| WO | WO 99/26567 A1 | 6/1999 |
| WO | WO 99/30641 A1 | 6/1999 |
| WO | WO 99/38470 A2 | 8/1999 |
| WO | WO 99/38470 A3 | 8/1999 |
| WO | WO 00/13627 A1 | 3/2000 |
| WO | WO 00/64369 A1 | 11/2000 |
| WO | WO 00/64390 A1 | 11/2000 |
| WO | WO 00/64391 A1 | 11/2000 |
| WO | WO 00/64393 A1 | 11/2000 |
| WO | WO 00/72788 A1 | 12/2000 |
| WO | WO 01/50943 A2 | 7/2001 |
| WO | WO 01/78631 A2 | 10/2001 |
| WO | WO 01/78656 A2 | 10/2001 |
| WO | WO 01/85065 | 11/2001 |
| WO | WO 02/074052 A2 | 9/2002 |
| WO | WO 03/015659 A2 | 2/2003 |
| WO | WO 03/041622 | 5/2003 |
| WO | WO 03/045290 A1 | 6/2003 |
| WO | WO 03/073968 A2 | 9/2003 |

OTHER PUBLICATIONS

Phillip C. Jacobi, MD, Thomas S. Dletleln, MD and Gunter K. Krieglstein, MD, *Bimanual Trabecular Aspiration in Pseudoexfoliation Glaucoma, Ophthalmology, 1998*, vol. 105, No. 5, May 1998, pp. 886-894.

Phillip C. Jacobi, MD, Thomas S. Dietleln, MD and Gunter K. Krieglstein, MD, *Microendoscopic Trabecular Surgery in Glaucoma Management, Ophthalmology, 1999* vol. 106, No. 3, pp. 538-544.

Arthur L. Schwartz, MD, & Douglas R. Anderson, MD, *Trabecular Surgery, Arch Ophthalmol.* vol. 92, Aug. 1974, pp. 134-138.

R.A. Hill, Q. Ren, D.C. Nguyen, L.H. Liaw, & M.W. Berns, *Free-Electron Laser (FEL) Ablation of Ocular Tissues, Laser Med Sci 1998,* vol. 13, pp. 219-226.

Maurice H. Luntz, MD & D.G. Livingston, B.SC., *Trabeculotomy AB Externo & Trabeculectomy in Congenital and Adult-Onset Glaucoma, American Journal of Ophthalmology,* Feb. 1977. vol. 83, No. 2, pp. 174-179.

W.M. Grant, MD, *Further Studies on Facllity of Flow Through the Trabecular Meshwork, AMA Archives of Ophthalmology,* Oct. 1958, vol. 60, pp. 523-533.

Richard A. Hill, MD, George Baerveldt, MD, Serdar A. Ozler, MD, Michael Pickford, BA, Glen A. Profeta, BS, & Michael W. Berns, PhD, *Laser Trabecular Ablation (LTA), Laser in Surgery and Medicine,* 1991, vol. 11, pp. 341-346.

Detliev Spiegal, MD, Karin Kobuch, MD, Richard A. Hill, MD, Ronald L. Gross, MD, *Schlemm's Canal Implant: A New Method to Lower Intraocular Pressure in Patients With POAG, Opthalmic Surgery and Lasers,* Jun. 1999, vol. 39, No. 6, pp. 492-494.

(56) References Cited

OTHER PUBLICATIONS

L. Jay Katz, MD,, *A Call for Innovative Operations for Glaucoma*, Arch Ophthalmology, Mar. 2000, vol. 118, pp. 412-413.

Anselm Kampik & Franz Grehn, *Nutzen und Risiken Augenärzticher Therapie, Hauptreferate der XXXIII, Essener Fortbildung für Augenärzte*, Dec. 1998. (English translated version provided "Benefits and Risks of Ophthalmological Therapy").

Detlev Spiegel, *7 Chirurglsche Glaukomtherapie*, pp. 79-88 (English translation provided).

Rosenberg, et al., "Implants in Glaucoma Surgery", The Glaucomas, 1996, Chapter 88, pp. 1783-1807 (27 pages).

Hans Hoerauf, Christopher Wirbelauer, Christian Scholz, Ralf Engelhardt, Peter Koch, Horst Laqua, and Reginald Birngruber, *Slit-lamp-adapted optical coherence tomography of the anterior segment*, Graefe's Arch Clin Exp Ophthalmol, 2000, vol. 238, pp. 8-18.

Sumita Radhakrishnan, Andrew M. Rollins, Jonathan E. Roth, S. Yazddanfar, Volker Westphal, David Bardenstein, and Joseph Izatt, *Real-Time Optical Coherence Tomography of the Anterior Segment at 1310 nm*, Arch Ophthalmology, Aug. 2001, vol. 119, pp. 1179-1185.

I. Grierson, R.C. Howes, and Q. Wang, *Age-related Changes in the Canal of Schlemm*, Exp. Eye Res., 1984, vol. 39, pp. 505-512.

Luanna K. Putney, Cecile Rose T. Vibat, and Martha E. O'Donnell, *Intracellular Cl Regulates Na-K-Cl Cotransport Activity in Human Trabecular Meshwork Cells*, 1999 American Physiological Society, Sep. 1999, pp. C373 through C383.

Edited by Kevin Strange, *Cellular and Molecular Physiology of Cell Volume Regulation*, Library of Congress Cataloging in-Publication Data, CRC Press, Inc., pp. 312-321.

William Tatton, Ruth M.E. Chalmers-Redman, Ajay Sud, Steven M. Podos, and Thomas Mittag, *Maintaining Mitochondrial Membrane Impermeability: An Opportunity for New Therapy in Glaucoma*, Survey of Ophthalmology, vol. 45, Supplement 3, May 2001, pp. S277 through S283.

Robert W. Nickells, *Apoptosis of Retinal Ganglion Cells in Glaucoma: An Update of the Molecular Pathways Involved in Cell Death*, Survey of Ophthalmology, vol. 43, Supplement 1, Jun. 1999, pp. S-151 through S-161.

Grune & Stratton, Harcourt Brace Jovanovich Publishers, edited by J.E. Cairns, *Glaucoma*, vol. 1, Chapter 14, *Anatomy of the Aqueous Outflow Channels*, by Johannes W. Rohen, pp. 277-296.

Yasuhiro Matsumoto and Douglas H. Johnson, *Trabecular Meshwork Phagocytosis in Graucomatous Eyes*, Ophthalmologica 1977, vol. 211, pp. 147-152.

M. Bruce Shields, MD, *A Study Guide for Glaucoma: Aqueous Humor Dynamics*, Copyright 1982, pp. 6-43.

M.A. Johnstone, R. Stegmann, and B.A. Smit, *American Glaucoma Society, 12th Annual Meeting, Cylindrical Tubular Structures Spanning from Trabecular Meshwork Across SC*, Laboratory Studies with SEM TEM and Tracers Correlated with Clinical Findings, p. 39.

W.G. Tatton, *Apoptotic Mechanisms in Neurodegeneration: Possible Relevance to Glaucoma*, European Journal of Ophthalmology, Jan.-Mar. 1999, vol. 9, Supplement 1, pp. S22 through S29.

Cindy K. Bahler, BS, Gregrory T. Smedley, PhD, Jianbo Zhou, PhD, Douglas H. Johnson, MD., *Trabecular Bypass Stents Decrease Intraocular Pressure in Cultured Human Anterior Segments*, American Journal of Ophthalmology, Dec. 2004, vol. 138, pp. 988-994.

Jianbo Zhou, PhD, Gregory T. Smedley, PhD., *A Trabecular Bypass Flow Hypothesis*, Feb. 2005, vol. 14 No. 1, pp. 74-83.

U.S. Appl. No. 09/452,963, filed Dec. 2, 1999. Title: *Expandable/Retractable Stent for Venous and Valvular Annulus Use*.

Vincente, L. Jocson, M.D.; *Air Trabeculotomy*; American Journal of Ophthalmolgy: vol. 79, No. 1, Jan.-Jun. 1975; pp. 107-111.

Daniel A. Fletcher, Ph.D., Daniel V. Palanker, Ph.D., Philip Hule, M.D., Jason Miller, MS, Michael F. Marmor, M.D. And Mark S. Blumenkranz, M.D.; *Intravascular Drug Delivery With a Pulsed Liquid Microjet;* (Reprinted) Arch Ophthalmology; vol. 120, Sep. 2002, pp. 1206-1208.

Troncoso, Manuel U., Tantalum implants for inducing hypotony, American Journal of Ophthalmology, vol. 32, No. 4, Apr. 1949, pp. 499-508 (11 pages).

\* cited by examiner

IMPLANT DELIVERY SYSTEM AND METHODS THEREOF FOR TREATING OCULAR DISORDERS

RELATED APPLICATIONS

This application is a continuation of U.S. application Ser. No. 10/231,342, filed Aug. 28, 2002, now U.S. Pat. No. 7,331,984 B2, issued Feb. 19, 2008, which claims the benefit of U.S. Provisional Application No. 60/315,463, filed Aug. 28, 2001, entitled "GLAUCOMA SHUNT FOR AB INTERNO USE" and U.S. Provisional Application No. 60/363,980, filed Mar. 14, 2002, entitled "MEANS AND PROCEDURES FOR IMPLANTING A GLAUCOMA SHUNT AB INTERNO", the entirety of each one of which is hereby incorporated by reference herein.

BACKGROUND OF THE INVENTION

Field of the Invention

The invention generally relates to improved medical devices and methods for the reduction of elevated pressure in organs of the human body. More particularly, the invention relates to the treatment of glaucoma by trabecular bypass surgery, which is a means for using an implant or stent, such as a micro stent, shunt or the like, to bypass diseased trabecular meshwork at the level of trabecular meshwork and use/restore existing outflow pathways.

Description of the Related Art

About two percent of people in the United States have glaucoma. Glaucoma is a group of eye diseases that causes pathological changes in the optic disk and corresponding visual field loss resulting in blindness if untreated. Intraocular pressure elevation is the major etiologic factor in all glaucomas.

In glaucomas associated with an elevation in eye pressure the source of resistance to outflow is in the trabecular meshwork. The tissue of the trabecular meshwork allows the "aqueous" to enter Schlemm's canal, which then empties into aqueous collector channels in the posterior wall of Schlemm's canal and then into aqueous veins. The aqueous or aqueous or is a transparent liquid that fills the region between the cornea at the front of the eye and the lens. The aqueous humor is constantly secreted by the ciliary body around the lens, so there is a continuous flow of the aqueous humor from the ciliary body to the eye's front chamber.

The eye's pressure is determined by a balance between the production of aqueous and its exit through the trabecular meshwork (major route) or via uveal sclera outflow (minor route). The trabecular meshwork is located between the outer rim of the iris and the internal periphery of the cornea. The portion of the trabecular meshwork adjacent to Schlemm's canal causes most of the resistance to aqueous outflow (juxtacanilicular meshwork).

Glaucoma is grossly classified into two categories: closed-angle glaucoma and open-angle glaucoma. Closed-angle glaucoma is caused by closure of the anterior angle by contact between the iris and the inner surface of the trabecular meshwork. Closure of this anatomical angle prevents normal drainage of aqueous humor from the anterior chamber of the eye.

Open-angle glaucoma is any glaucoma in which the angle of the anterior chamber remains open, but the exit of aqueous through the trabecular meshwork is diminished. The exact cause for diminished filtration is unknown for most cases of open-angle glaucoma. However, there are secondary open-angle glaucomas that may include edema or swelling of the trabecular spaces (from steroid use), abnormal pigment dispersion, or diseases such as hyperthyroidism that produce vascular congestion.

All current therapies for glaucoma are directed at decreasing intraocular pressure. This is initially by medical therapy with drops or pills that reduce the production of aqueous humor or increase the outflow of aqueous. However, these various drug therapies for glaucoma are sometimes associated with significant side effects, such as headache, blurred vision, allergic reactions, death from cardiopulmonary complications and potential interactions with other drugs. When the drug therapy fails, surgical therapy is used.

Surgical therapy for open-angle glaucoma utilizes laser (trabeculoplasty), trabeculectomy and aqueous shunting implants after failure of trabeculectomy or if trabeculectomy is unlikely to succeed. Trabeculectomy is a major surgery that is most widely used and is augmented with topically applied anticancer drugs such as 5-flurouracil or mitomycin-c to decrease scarring and increase surgical success.

Approximately 100,000 trabeculectomies are performed on Medicare age patients per year in the United States. This number would increase if the morbidity associated with trabeculectomy could be decreased. The current morbidity associated with trabeculectomy includes failure (about 10-15%), infection (a life long risk of about 2-5%), choroidal hemorrhage (about 1%, a severe internal hemorrhage from pressure too low resulting in a visual loss), cataract formation, and hypotony maculopathy (potentially reversible visual loss from pressure too low).

If it were possible to bypass the local resistance to outflow of aqueous at the point of the resistance and use existing outflow mechanisms, surgical morbidity would greatly decreased. The reason for this is that the episcleral aqueous veins have a backpressure that would prevent the eye pressure from going too low. This would substantially eliminate the risk of hypotony maculopathy and choroidal hemorrhage. Furthermore, visual recovery would be very rapid and risk of infection would be very small (a reduction from about 2-5% to about 0.05%). Because of these reasons surgeons have tried for decades to develop a workable surgery for the trabecular meshwork.

The previous techniques, which have been tried, are goniotomy/trabeculotomy, and other mechanical disruption of the trabecular meshwork, such as trabeculopuncture, goniophotoablation, laser trabecular ablation and goniocurretage. These are briefly described below.

Goniotomy/Trabeculotomy:

Goniotomy and trabeculotomy are simple and directed techniques of microsurgical dissection with mechanical disruption of the trabecular meshwork. These initially had early favorable responses in the treatment of open-angle glaucoma. However, long-term review of surgical results showed only limited success in adults. In retrospect, these procedures probably failed secondary to repair mechanisms and a process of "filling in". The filling in is the result of a healing process which has the detrimental effect of collapsing and closing in of the created opening throughout the trabecular meshwork. Once the created openings close, the pressure builds back up and the surgery fails.

Trabeculopuncture:

Q-switched Neodymiun (Nd):YAG lasers also have been investigated as an optically invasive technique for creating full-thickness holes in trabecular meshwork. However, the relatively small hole created by this trabeculopuncture technique exhibits a filling in effect and fails.

Goniophotoablation/Laser Trabecular Ablation:

Goniophotoablation is disclosed by Berlin in U.S. Pat. No. 4,846,172, and describes the use of an excimer laser to treat glaucoma by ablating the trabecular meshwork. This was not demonstrated by clinical trial to succeed. Hill et al. used an Erbium:YAG laser to create full thickness holes through trabecular meshwork (Hill et al., Lasers in Surgery and Medicine 11:341-346, 1991). This technique was investigated in a primate model and a limited human clinical trial at the University of California, Irvine. Although morbidity was zero in both trials, success rates did not warrant further human trials. Failure again was from filling in of created defects in trabecular meshwork by repair mechanisms. Neither of these is a valid surgical technique for the treatment of glaucoma.

Goniocurretage:

This is an ab-interno (from the inside) mechanical disruptive technique. This uses an instrument similar to a cyclodialysis spatula with a microcurrette at the tip. Initial results are similar to trabeculotomy that fails secondary to repair mechanisms and a process of filling in.

Although trabeculectomy is the most commonly performed filtering surgery, Viscocanulostomy (VC) and non-penetrating trabeculectomy (NPT) are two new variations of filtering surgery. These are ab-externo (from the outside), major ocular procedures in which Schlemm's canal is surgically exposed by making a large and very deep scleral flap. In the VC procedure, Schlemm's canal is cannulated and a viscoelastic drug injected (which dilates Schlemm's canal and the aqueous collector channels). In the NPT procedure, the inner wall of Schlemm's canal is stripped off after surgically exposing the canal.

Trabeculectomy, VC, and NPT are performed under a conjunctival and scleral flap, such that the aqueous humor is drained onto the surface of the eye or into the tissues located within the lateral wall of the eye. Normal physiological outflows are not used. These surgical operations are major procedures with significant ocular morbidity. When Trabeculectomy, VC, and NPT are thought to have a low chance for success, a number of implantable drainage devices have been used to ensure that the desired filtration and outflow of aqueous humor through the surgical opening will continue. The risk of placing a glaucoma drainage implant also includes hemorrhage, infection and postoperative double vision that is a complication unique to drainage implants.

Examples of implantable shunts or devices for maintaining an opening for the release of aqueous humor from the anterior chamber of the eye to the sclera or space underneath conjunctiva have been disclosed in U.S. Pat. No. 6,007,511 (Prywes), U.S. Pat. No. 6,007,510 (Nigam), U.S. Pat. No. 5,893,837 (Eagles et al.), U.S. Pat. No. 5,882,327 (Jacob), U.S. Pat. No. 5,879,319 (Pynson et al.), U.S. Pat. No. 5,807,302 (Wandel), U.S. Pat. No. 5,752,928 (de Roulhac et al.), U.S. Pat. No. 5,743,868 (Brown et al.), U.S. Pat. No. 5,704,907 (Nordquist et al.), U.S. Pat. No. 5,626,559 (Solomon), U.S. Pat. No. 5,626,558 (Suson), U.S. Pat. No. 5,601,094 (Reiss), RE. 35,390 (Smith), U.S. Pat. No. 5,558,630 (Fisher), U.S. Pat. No. 5,558,629 (Baerveldt et al.), U.S. Pat. No. 5,520,631 (Nordquist et al.), U.S. Pat. No. 5,476,445 (Baerveldt et al.), U.S. Pat. No. 5,454,796 (Krupin), U.S. Pat. No. 5,433,701 (Rubinstein), U.S. Pat. No. 5,397,300 (Baerveldt et al.), U.S. Pat. No. 5,372,577 (Ungerleider), U.S. Pat. No. 5,370,607 (Memmen), U.S. Pat. No. 5,338,291 (Speckman et al.), U.S. Pat. No. 5,300,020 (L'Esperance, Jr.), U.S. Pat. No. 5,178,604 (Baerveldt et al.), U.S. Pat. No. 5,171,213 (Price, Jr.), U.S. Pat. No. 5,041,081 (Odrich), U.S. Pat. No. 4,968,296 (Ritch et al.), U.S. Pat. No. 4,936,825 (Ungerleider), U.S. Pat. No. 4,886,488 (White), U.S. Pat. No. 4,750,901 (Molteno), U.S. Pat. No. 4,634,418 (Binder), U.S. Pat. No. 4,604,087 (Joseph), U.S. Pat. No. 4,554,918 (White), U.S. Pat. No. 4,521,210 (Wong), U.S. Pat. No. 4,428,746 (Mendez), U.S. Pat. No. 4,402,681 (Haas et al.), U.S. Pat. No. 4,175,563 (Arenberg et al.) and U.S. Pat. No. 4,037,604 (Newkirk).

All of the above techniques and variations thereof have numerous disadvantages and moderate success rates. They involve substantial trauma to the eye and require great surgical skill by creating a hole over the full thickness of the sclera/cornea into the subconjunctival space. Furthermore, normal physiological outflow pathways are not used. The procedures are mostly performed in an operating room generating a facility fee, anesthesiologist's professional fee and have a prolonged recovery time for vision. The complications of filtration surgery have inspired ophthalmic surgeons to look at other approaches to lowering intraocular pressure.

SUMMARY OF THE INVENTION

The trabecular meshwork and juxtacanilicular tissue together provide the majority of resistance to the outflow of aqueous and, as such, are logical targets for surgical removal in the treatment of open-angle glaucoma. In addition, minimal amounts of tissue are altered and existing physiologic outflow pathways are utilized. Trabecular bypass surgery has the potential for much lower risks of choroidal hemorrhage, infection and uses existing physiologic outflow mechanisms. This surgery could be performed under topical anesthesia in a physician's office with rapid visual recovery.

International PCT Publication No. WO 01/78631, published Oct. 25, 2001 (Appl. No. PCT/US01/07398, filed Mar. 8, 2001), by some co-inventor(s) of this patent application, entitled "APPARATUS AND METHOD FOR TREATING GLAUCOMA", the entire contents of which are hereby incorporated by reference herein, discloses a seton implant positioned through the trabecular meshwork so that an inlet end of the seton implant is exposed to the anterior chamber of the eye and an outlet end is positioned into Schlemm's canal at about an exterior surface of the trabecular meshwork for permitting aqueous humor to flow out of the anterior chamber. An ab interno microsurgery for creating an opening in the trabecular meshwork.

International PCT Publication No. 01/97727, published Dec. 27, 2001 (Appl. No. PCT/US01/18541, filed Jun. 6, 2001), by some co-inventor(s) of this patent application, entitled "STENTED TRABECULAR SHUNT AND METHODS THEREOF", the entire contents of which are hereby incorporated by reference herein, discloses a stented trabecular shunt comprising an outlet section that is expandable and adapted for stabilizing within Schlemm's canal with an ab interno microsurgery for creating an opening in the trabecular meshwork.

International PCT Publication No. 02/36052, published May 10, 2002 (Appl. No. PCT/US01/14783, filed May 8, 2001), by some co-inventor(s) of this patent application, entitled "GLAUCOMA TREATMENT DEVICE", the entire contents of which are hereby incorporated by reference herein, discloses a device for directing the flow of aqueous humor through the lumen to Schlemm's canal with an ab interno microsurgery for creating an opening in the trabecular meshwork.

The ab interno microsurgery disclosed in the above WIPO PCT publications/applications has a common disadvantage of first using a piercing instrument for creating an opening in the trabecular meshwork. The piercing instrument goes into the anterior chamber, creates an opening in the trabecular meshwork and is then withdraw from the anterior chamber before a trabecular stent is implanted in a separate insertion. Therefore, there is a great clinical need for the treatment of glaucoma by a trabecular bypass surgery using a micro stent to bypass deficient trabecular meshwork in a one-step simple procedure. One object of the invention is to provide a trabecular stent and methods for treating elevated intraocular pressure with an ab interno microsurgery for creating an opening in the trabecular meshwork by a piercing member of the applicator slidably through the lumen of the stent in a combined piercing and stent implanting one-step inserting procedure.

In some preferred embodiments, the stent has an inlet portion configured to extend through a portion of the trabecular meshwork of an eye, and an outlet portion configured to extend into Schlemm's canal of the eye, wherein the outlet portion may have a lumen with an oval cross-section having a long axis.

The outlet portion in certain embodiments has a longitudinal axis, such that the long axis of the oval cross-section and the longitudinal axis of the outlet portion define a plane, the inlet portion having a longitudinal axis which lies outside the plane at an angle thereto.

In some preferred arrangements, the stent comprises an inlet portion configured to extend through a portion of the trabecular meshwork, an outlet portion configured to extend into Schlemm's canal, and at least one protrusion on the outlet portion configured to exert traction against an inner surface of Schlemm's canal. This protrusion can comprise at least one barb or ridge.

Some preferred embodiments comprise an inlet portion configured to extend through a portion of the trabecular meshwork, an outlet portion configured to extend into Schlemm's canal, and a one-way leaflet type valve within the inlet and/or outlet portions.

Some aspects relate to a method for delivering a stent within an eye. The method generally comprising providing an elongate applicator having a piercing member intended to pass through the lumen of the stent, advancing a distal end of the applicator with the piercing member through at least a portion of the trabecular meshwork of the eye, retrieving the piercing member, advancing the stent along the applicator toward the distal end, and the positioning the stent to conduct aqueous humor between the anterior chamber of the eye and Schlemm's canal.

In certain embodiments, the advancing of the applicator comprises advancing it from the anterior chamber into the trabecular meshwork. In further embodiments, the positioning comprises positioning an end of the stent within Schlemm's canal adjacent to an aqueous collection channel.

Certain preferred embodiments include an apparatus for delivering a stent to the anterior chamber of an eye comprising an elongate applicator having a lumen, an outer surface, and a distal end; a removable, elongate piercing member within the lumen of the applicator; a slidable stent delivery mechanism configured to permit the stent to be advanced and to be positioned in about the trabecular meshwork of the eye. The piercing member is positioned at the distal end of the applicator, wherein the piercing member is slidably advanceable through the lumen of the stent. The piercing member can be selected from the group consisting of a knife, a laser probe, a pointed guide member, and an energy source, such as radiofrequency (RF), ultrasonic energy, fiber optic laser, microwave, focused ultrasound and the like. The apparatus can also further comprise an opening in the outer surface of the applicator configured to allow fluid infusion into the eye.

In further preferred embodiments, an apparatus for delivering a stent in an eye comprises an elongate applicator member adapted for insertion into an anterior chamber of the eye, the elongate member having a distal end portion configured to retain the stent therein, the distal end portion comprising a piercing member configured to form an opening in the trabecular meshwork of the eye for receipt of the stent, such that one end of the stent is in Schlemm's canal. The elongate applicator member can further comprise a lumen which conducts fluid toward the distal end portion.

Some preferred embodiments provide further surgical treatment of glaucoma (trabecular bypass surgery) at the level of trabecular meshwork and restore existing physiological outflow pathways. An implant bypasses diseased trabecular meshwork at the level of trabecular meshwork and which restores existing physiological outflow pathways. The implant has an inlet end, an outlet end and a lumen therebetween. The inlet end is positioned in the anterior chamber at the level of the internal trabecular meshwork and the outlet end is positioned at about the exterior surface of the diseased trabecular meshwork and/or into fluid collection channels of the existing outflow pathways.

In accordance with some preferred methods, trabecular bypass surgery creates an opening or a hole through the diseased trabecular meshwork through minor microsurgery. To prevent "filling in" of the hole, a biocompatible elongated implant is placed within the hole as a stent, which may include, for example, a hollow tube. In one exemplary embodiment, the stent implant may be positioned across the diseased trabecular meshwork alone and it does not extend into the eye wall or sclera. In another embodiment, the inlet end of the implant is exposed to the anterior chamber of the eye while the outlet end is positioned at the exterior surface of the trabecular meshwork. In another exemplary embodiment, the outlet end is positioned at and over the exterior surface of the trabecular meshwork and into the fluid collection channels of the existing outflow pathways. In still another embodiment, the outlet end is positioned in the Schlemm's canal. In a modified embodiment, the outlet end enters into fluid collection channels up to the level of the aqueous veins or episcleral aqueous veins.

According to some preferred embodiments, the stent implant is made of biocompatible material, which is either hollow or porous to allow the flow of aqueous humor or solid biocompatible material that imbibes aqueous. The material for the stent may be selected from the group consisting of porous material, semi-rigid material, soft material, hydrophilic material, hydrophobic material, hydrogel, elastic material, and the like.

The trabecular stent, particularly the porous stent, may have high water affinity that hydrophilic and tissue compatible. One or more drugs may be loaded onto the trabecular stent and slowly released to the surrounding tissue effective to treat glaucoma and/or other opthalmology abnormalities.

In accordance with further preferred embodiments, the stent implant may be rigid or it may be made of relatively soft material and is somewhat curved at its distal section to fit into the existing physiological outflow pathways, such as Schlemm's canal. The distal section inside the outflow pathways may have an oval shape to stabilize the stent in place without undue suturing. Stabilization or retention of the stent may be further strengthened by a tapered end and/or by at least one ridge or rib on the exterior surface of the distal section of the stent, or other surface alterations designed to retain the stent.

In some embodiments, the stent may include a micropump, one-way valve, or semi-permeable membrane if reflux of red blood cells or serum protein becomes a clinical problem. It may also be useful to use a biocompatible material that hydrates and expands after implantation so that the stent is locked into position around the trabecular meshwork opening or around the distal section of the stent.

One of the advantages of trabecular bypass surgery, as disclosed herein, and the use of a stent implant to bypass diseased trabecular meshwork at the level of trabecular meshwork and thereby use existing outflow pathways is that the treatment of glaucoma is substantially simpler than in existing therapies. A further advantage of some preferred embodiments is the utilization of simple microsurgery that may be performed on an outpatient basis with rapid visual recovery and greatly decreased morbidity. Finally, a distinctly different approach is used than is found in existing implants. Physiological outflow mechanisms are used or re-established by the implant of some preferred embodiments, in contra-distinction with previously disclosed methodologies.

Some aspects of the invention provide a trabecular stent to be inserted through an opening of the deficient trabecular meshwork, wherein the opening is created by using a cutting instrument slid inside a lumen of the trabecular stent in a combined one-step cutting and implanting inserting operation.

Some other aspects of the invention provide a method for cleaning the obstructed lumen of a trabecular stent by an applicator that has a piercing member that is slidably advanceable approaching or through the obstructed lumen of the stent.

For purposes of summarizing the invention, certain aspects, advantages and novel features of the invention have been described herein above. Of course, it is to be understood that not necessarily all such advantages may be achieved in accordance with any particular embodiment of the invention. Thus, the invention may be embodied or carried out in a manner that achieves or optimizes one advantage or group of advantages as taught or suggested herein without necessarily achieving other advantages as may be taught or suggested herein.

All of these embodiments are intended to be within the scope of the invention herein disclosed. These and other embodiments of the invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and some of its features and advantages, certain preferred embodiments and modifications thereof will become apparent to those skilled in the art from the detailed description herein having reference to the figures that follow, of which.

DETAILED DESCRIPTION OF THE PREFERRED EMBODIMENTS

The drawings generally illustrate a method for the treatment of glaucoma by trabecular bypass surgery. In particular, a stent implant is used to bypass diseased or deficient trabecular meshwork at the level of trabecular meshwork to use or restore existing outflow pathways and methods thereof are disclosed.

While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompass by the general concepts described herein and below.

Figure 1:
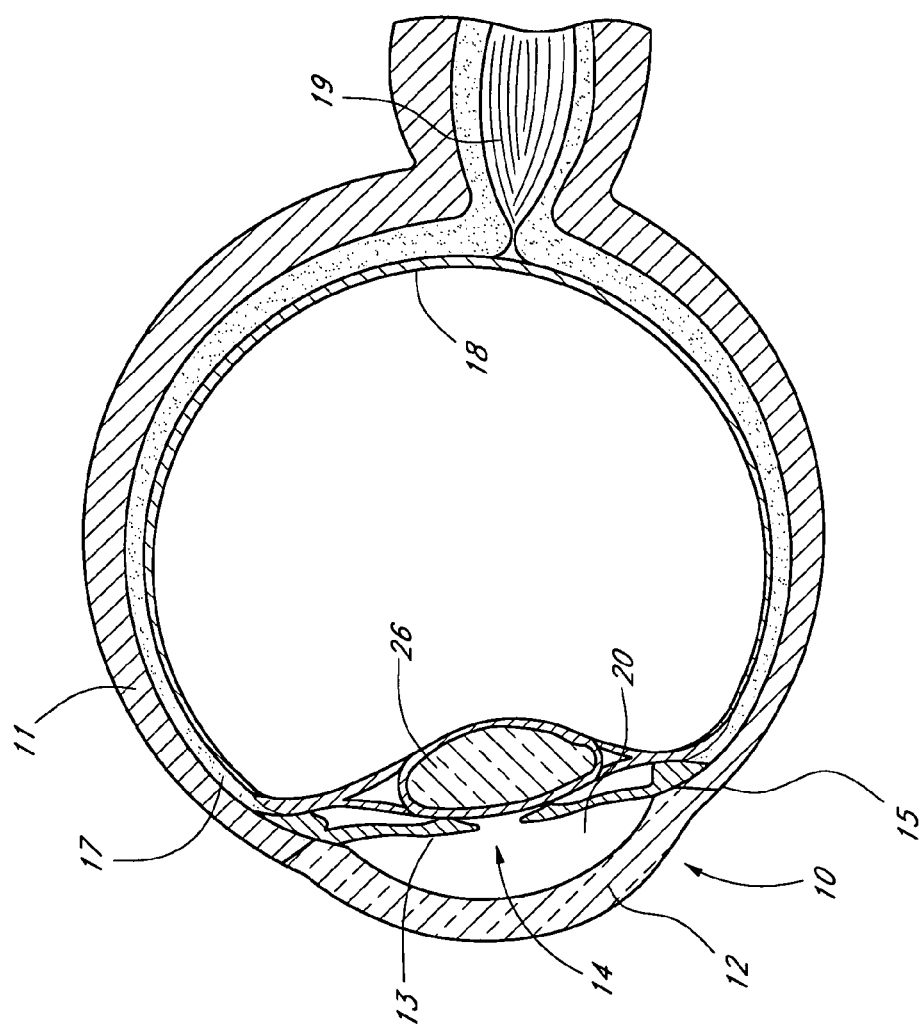
FIG. 1 is a sectional view of an eye for illustration purposes.
Figure 2:
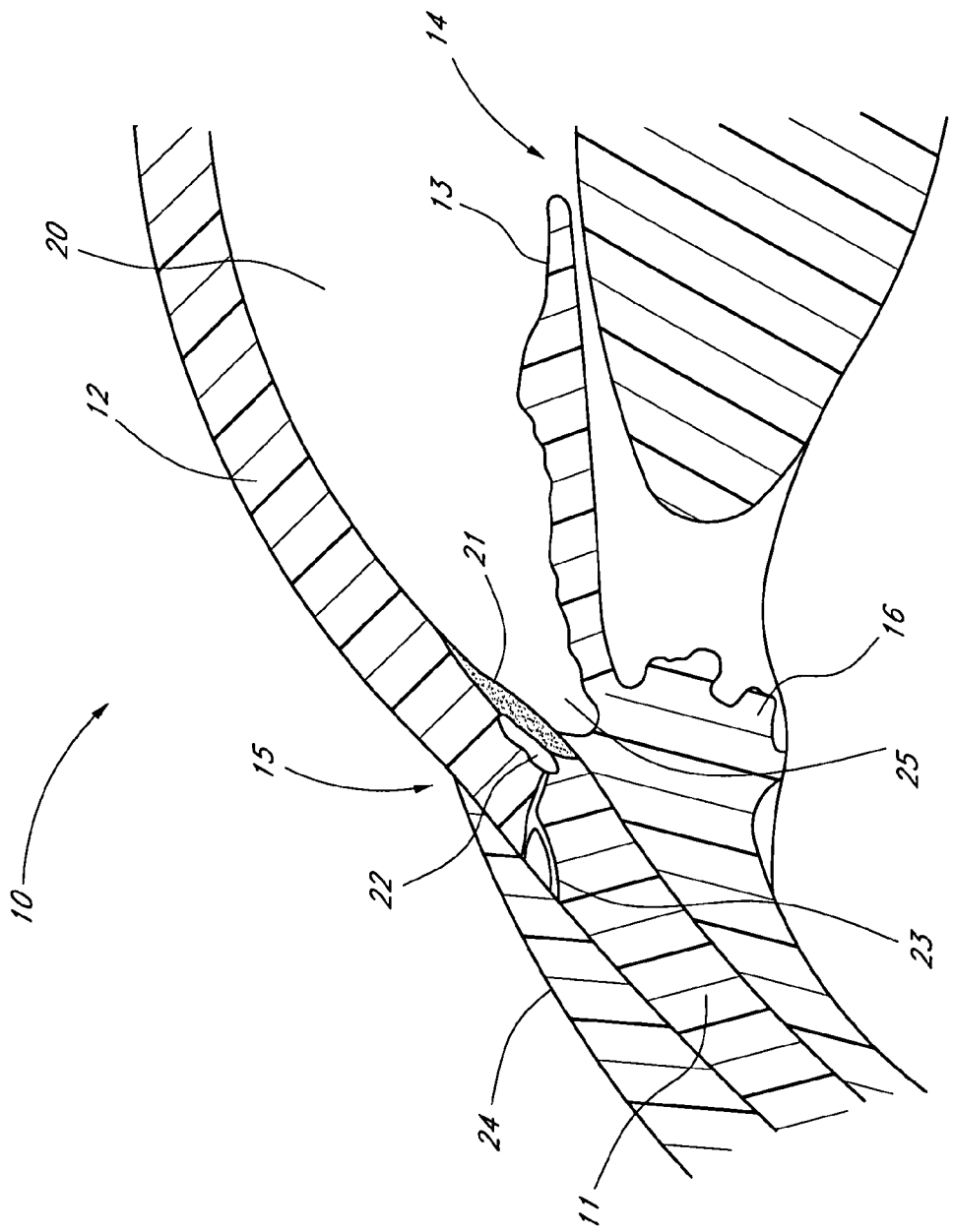
FIG. 2 is a close-up sectional view showing the anatomical diagram of trabecular meshwork and the anterior chamber of the eye of FIG. 1.

For background illustration purposes, FIG. 1 shows a sectional view of an eye 10, while FIG. 2 shows a close-up view, showing the relative anatomical locations of a trabecular meshwork 21, an anterior chamber 20, and Schlemm's canal 22. Thick collagenous tissue known as sclera 11 covers the entire eye 10 except that portion covered by the cornea 12. The cornea 12 is a thin transparent tissue that focuses and transmits light into the eye and through a pupil 14 which is a circular hole in the center of an iris 13 (colored portion of the eye). The cornea 12 merges into the sclera 11 at a juncture referred to as a limbus 15. A ciliary body 16 begins internally in the eye and extends along the interior of the sclera 11 and is coextensive with a choroid 17. The choroid 17 is a vascular layer of the eye, located between the sclera 11 and an underlying retina 18. An optic nerve 19 transmits visual information to the brain and is the anatomic structure that is progressively destroyed by glaucoma.

The anterior chamber 20 of the eye 10 (FIGS. 1 and 2), which is bound anteriorly by the cornea 12 and posteriorly by the iris 13 and a lens 26, is filled with aqueous humor (also herein referred to as "aqueous"). Aqueous is produced primarily by the ciliary body 16 and reaches an anterior chamber angle 25, formed between the iris 13 and the cornea 12, through the pupil 14.

Referring in particular to FIGS. 1 and 2, in a normal eye, aqueous is removed from the anterior chamber 20 through the trabecular meshwork 21. Aqueous passes through trabecular meshwork 21 into Schlemm's canal 22 and thereafter through a plurality of aqueous veins 23, which merge with blood-carrying veins, and into systemic venous circulation. Intraocular pressure (IOP) of the eye 10 is maintained by an intricate balance between secretion and outflow of aqueous in the manner described above. Glaucoma is, in most cases, characterized by an excessive buildup of aqueous fluid in the anterior chamber 20 which leads to an increase in intraocular pressure. Fluids are relatively incompressible, and thus intraocular pressure is distributed relatively uniformly throughout the eye 10.

As shown in FIG. 2, the trabecular meshwork 21 is adjacent a small portion of the sclera 11. Exterior to the sclera 11 is a conjunctiva 24. Traditional procedures that create a hole or opening for implanting a device through the tissues of the conjunctiva 24 and sclera 11 involve extensive surgery, as compared to surgery for implanting a device through the trabecular meshwork 21, as described herein, which ultimately resides entirely within the confines of the sclera 11 and cornea 12.

Surgical methods and related medical devices for treating glaucoma are disclosed. The method comprises trabecular bypass surgery, which involves bypassing diseased trabecular meshwork with the use of a stent implant. The stent implant is inserted into an opening created in the trabecular meshwork by a piercing member that is slidably advanceable through the lumen of the stent implant for supporting the implant insertion. The stent implant is positioned through the trabecular meshwork so that an inlet end of the stent implant is exposed to the anterior chamber of the eye and an outlet end is positioned into fluid collection channels at about an exterior surface of the trabecular meshwork or up to the level of aqueous veins.

Some embodiments relate to a method of increasing aqueous humor outflow in an eye of a patient to reduce the intraocular pressure (IOP) therein. In one embodiment, the method comprises bypassing diseased or deficient trabecular meshwork at the level of the trabecular meshwork and thereby restoring existing outflow pathways. In another embodiment, the method comprises bypassing diseased trabecular meshwork at a level of the trabecular meshwork with a stent implant and using existing outflow pathways.

Stent Implant

Figure 3:
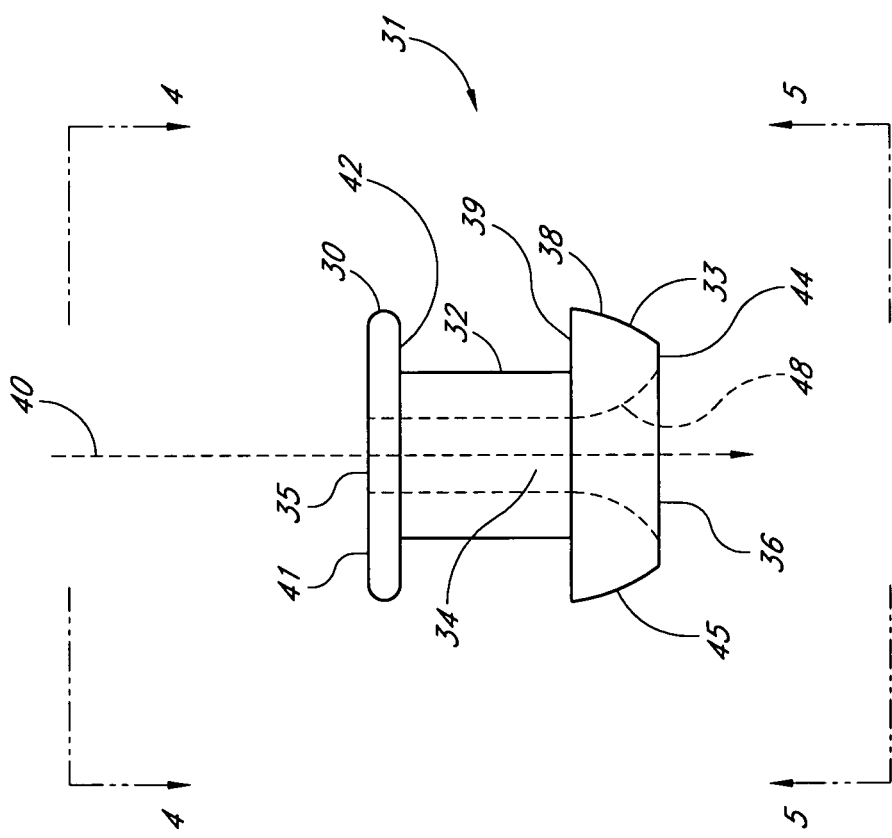
FIG. 3 is front elevation view of a stent implant having features and advantages in accordance with one embodiment of the invention.
Figure 4:
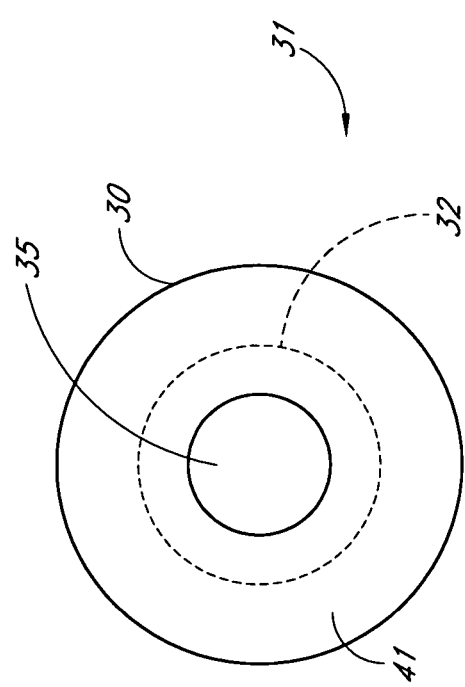
FIG. 4 is a top plan view of the stent implant of FIG. 3 along line 4-4 of FIG. 3.
Figure 5:
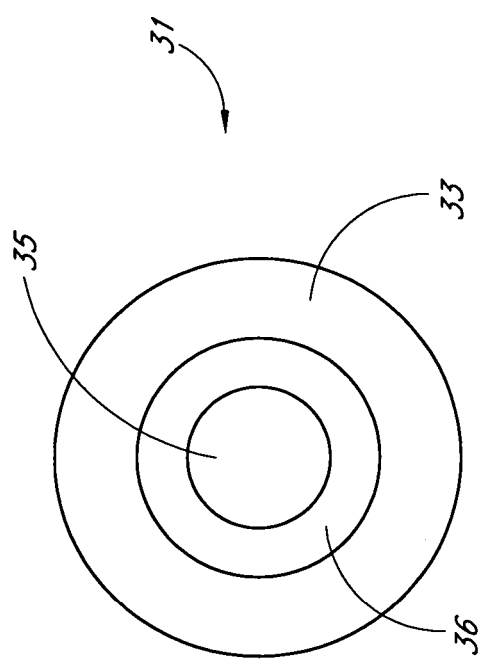
FIG. 5 is a bottom end view of the stent implant of FIG. 3 along line 5-5 of FIG. 3.
Figure 6:
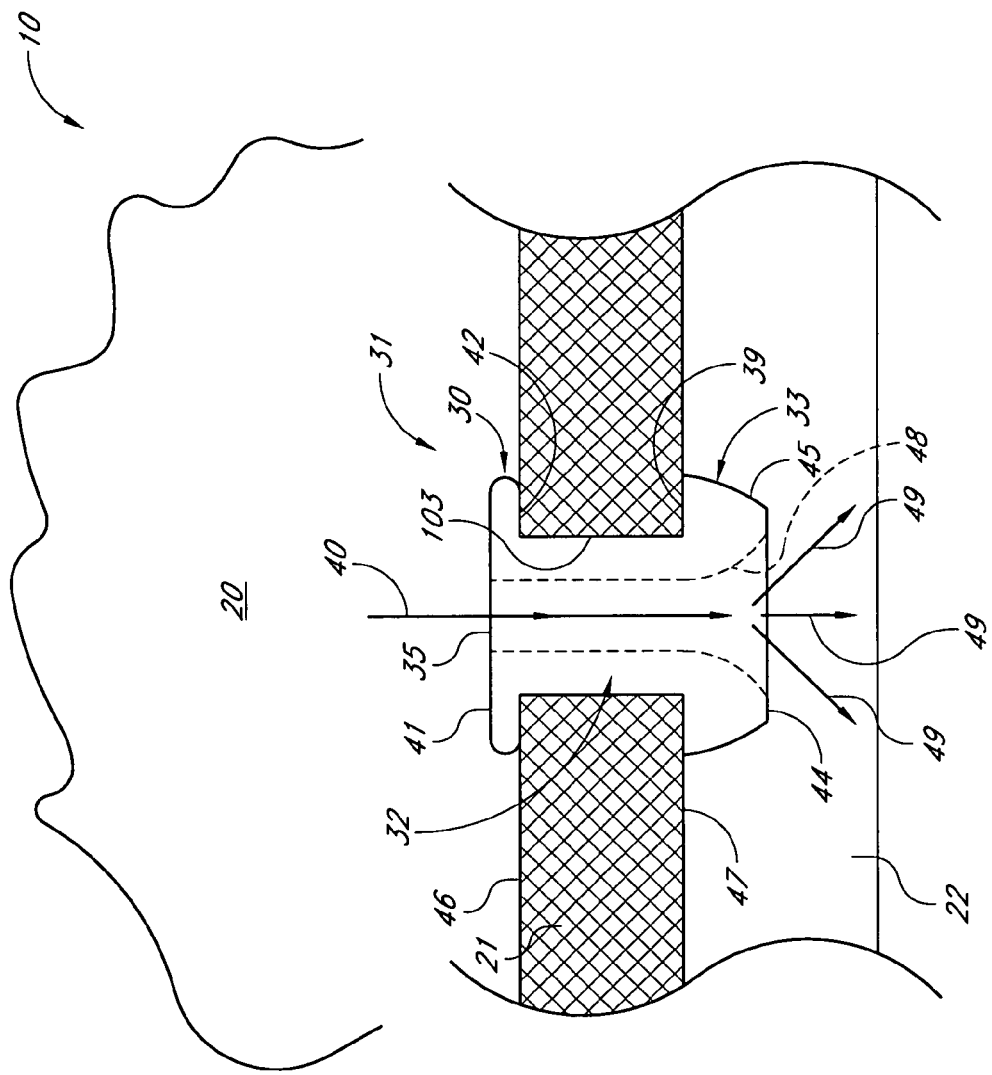
FIG. 6 is a simplified schematic illustration of the stent implant of FIG. 3 implanted within the eye having features and advantages in accordance with one embodiment of the invention.

FIGS. 3-5 show different views of a stent implant 31 constructed in accordance with one embodiment. FIG. 6 illustrates the implantation of the stent 31 within the eye 10. The stent implant 31 may comprise an elongated stent or other appropriate shape, size or configuration. In the illustrated embodiment, the stent implant 31 is in the form an elongated tubular element and generally comprises an inlet or proximal section 30 an outlet or distal section 33, a medial section 32 therebetween and a lumen or passage 34 extending therethrough.

Referring in particular to FIGS. 3-6, and as best seen in FIG. 6, in use, the inlet section 30 is positioned in the anterior chamber 20 of the eye 10 at about an interior surface 46 of the trabecular meshwork 21 and the outlet end or the outlet section 33 is positioned at about an exterior surface 47 of the diseased trabecular meshwork 21. As illustrated in FIG. 6, the trabecular meshwork interior side or surface 46 faces the anterior chamber 20 and the trabecular meshwork exterior side or surface 47 faces Schlemm's canal 22.

In some embodiments, the outlet section 33 may be positioned into fluid collection channels of the existing outflow pathways. In some embodiments, the existing outflow pathways comprise Schlemm's canal 22. The outlet section 33 may be further positioned into fluid collection channels up to the level of the aqueous veins 23 (see FIG. 2) with the stent 31 inserted within the eye 10. In general, the stent implant may be an axisymmetric stent or other configuration suitable for use with the methods taught or suggested herein.

In the illustrated embodiment of FIGS. 3-6, the proximal inlet section or portion 30 is generally in the form of a circular disc and has a proximal-most end or upper surface 41 and a lower surface 42. In modified embodiments, the stent proximal section may be shaped in other suitable manners with efficacy, as needed or desired, for example, oval, ellipsoidal, and the like. As best seen in FIG. 6, when the stent 31 is implanted within the eye 10, the upper surface 41 is exposed to or within the anterior chamber 20 while the lower surface 42 is seated on or abuts against the interior surface 46 of the trabecular meshwork 21 to stabilize the implanted stent 31.

In the illustrated embodiment of FIGS. 3-6, the medial or middle section or portion 32 is generally cylindrical in shape and has a generally circular cross-section. In modified embodiments, the stent medial section may be shaped in other suitable manners with efficacy, as needed or desired, for example, oval, ellipsoidal, and the like. As best seen in FIG. 6, the stent 31 is implanted within the eye 10, the medial section 32 is received within an opening 103 within the trabecular meshwork 21. Preferably, the middle section 32 is configured sized to fit the opened region 103 of the trabecular meshwork 21.

In the illustrated embodiment of FIGS. 3-6, the distal outlet section or portion 33 has an upper surface 39, a distal-most end or surface 44 and a tapered or curved outer surface 45 therebetween. The outer periphery of the outlet section 33 is generally circumferential or circular in shape. In modified embodiments, the stent distal section may be shaped in other suitable manners with efficacy, as needed or desired, for example, oval, ellipsoidal, and the like.

As best seen in FIG. 6, when the stent 31 is implanted within the eye 10, the distal section 33 is received within Schlemm's canal 22 and the upper surface 39 abuts against the exterior surface 47 of the trabecular meshwork 21 to stabilize the implanted stent 31. The distal section 33 may have a bulged outlet end or protrusion 38 and/or other bulging or protruding retention device or mechanism for stabilizing the stent implant 31 inside the existing outflow pathways after implantation, for example, a barb, among others.

For stabilization purposes, the outer surface of the distal section 33 may comprise a stubbed surface, a ribbed surface, a surface with pillars, a textured surface, and the like, or a combination thereof. In some embodiments, the distal section 33 may be curved or bent at an angle with reference to the proximal section 30 and/or the medial section 32. For example, the stent implant my be substantially L-shaped or T-shaped with the proximal and/or medial sections comprising a snorkel portion extending through the trabecular meshwork 21 and the distal section extending within Schlemm's canal 22 and/or other aqueous outflow pathways. The angulations(s) may be substantially perpendicular, acute angled or obtuse angled, as needed or desired.

In the illustrated embodiment of FIGS. 3-6, the lumen 34 has an upper opening, orifice or port 35 at the proximal end 41 and a lower opening, orifice or port 35 at the distal end 44. The lumen 34 has a generally circumferential or circular cross-section with a tapered or curved surface 48 within the distal section 33. In modified embodiments, the stent lumen may be shaped in other suitable manners with efficacy, as needed or desired, for example, oval, ellipsoidal, and the like, or some other shape configured and adapted for effective aqueous entrance and transmission. In some embodiments, the stent implant 31 may have a plurality of lumens to facilitate multiple flow transportation, as needed or desired.

As best seen in FIG. 4, the lumen upper orifice 35 is generally circular or round in shape. In modified embodiments, the lumen upper orifice may be shaped in other suitable manners with efficacy, as needed or desired, for example, oval, ellipsoidal, and the like, or some other shape configured and adapted for effective aqueous entrance and transmission. The stent implant 31 may comprise one or more inlet openings 35 at the inlet section 30 to allow adequate outflow of aqueous, as needed or desired.

As best seen in FIG. 5, the lumen lower orifice 36 is generally circular or round in shape. In modified embodiments, the lumen lower orifice may be shaped in other suitable manners with efficacy, as needed or desired, for example, oval, ellipsoidal, and the like, or some other shape configured and adapted for effective aqueous transmission enabling to conform to the shape and size of the existing outflow pathways. This configuration and/or that of the distal section 44 may match the contour of Schlemm's canal 22 to stabilize the stent 31 with respect to the iris and cornea by preventing unexpected movement. The stent implant 31 may comprise one or more outlet ports 36 at the outlet section 33 to allow adequate outflow of aqueous, as needed or desired.

As best seen in FIG. 6, aqueous from the anterior chamber 20 enters the lumen 34 through orifice 35 and passes through the stent in a direction generally indicated by arrow 40 and exits through the lumen orifice 36 into Schlemm's canal 22 in a direction generally indicated by arrows 49. Advantageously, the stent implant 31 assists in facilitating the outflow of aqueous in an outward direction 40 through the stent 31 and into Schlemm's canal 22 and subsequently into the aqueous collectors and the aqueous veins 23 (see FIG. 2) so that the intraocular pressure (IOP) is balanced.

Preferably, the entire exposed surface of the stent 31 (FIGS. 3-6) is biocompatible and tissue compatible so that the interaction/irritation between its surface and the surrounding tissue or aqueous is minimized. In modified embodiments, selected portions or surfaces of the stent 31 may comprise a biocompatible and/or tissue compatible material, as needed or desired.

As the skilled artisan will readily appreciate, the stent implant 31 of the illustrated embodiment may be dimensioned in a wide variety of manners. In an exemplary embodiment, the stent implant 31 has a length between about 0.3 millimeters (mm) to about over 1 centimeter (cm), depending on the body cavity where the stent implant is to be implanted. The outside or outer diameter of the stent implant 31 may range from about 30 micrometers or microns (μm) to about 500 μm or more. The lumen diameter is preferably in the range between about 10 μm to about 150 μm or larger. In other embodiments, the stent implant 31 may be dimensioned in modified manners with efficacy, as required or desired, giving due consideration to the goals of achieving one or more of the benefits and advantages as taught or suggested herein.

In some embodiments, and as discussed further herein, a method is disclosed for increasing aqueous humor outflow in an eye of a patient to reduce an intraocular pressure therein. The method comprises (a) creating an opening in trabecular meshwork by a piercing member of an applicator, wherein the trabecular meshwork comprises an interior side and exterior side, the piercing member is slidably moveable through the lumen of the stent; (b) inserting a stent implant into the opening in the trabecular meshwork; and (c) transporting the aqueous humor by the stent implant to bypass the trabecular meshwork at the level of the trabecular meshwork from the interior side facing the anterior chamber to the exterior side facing Schlemm's canal of the trabecular meshwork.

In one embodiment, the stent implant 31 (FIGS. 3-6) comprises a biocompatible material, such as a medical grade silicone, for example, the material sold under the trademark Silastic™, which is available from Dow Corning Corporation of Midland, Mich., or polyurethane, which is sold under the trademark Pellethane™, which is also available from Dow Corning Corporation. In another embodiment, other biocompatible materials (biomaterials) may be used, such as polyvinyl alcohol, polyvinyl pyrolidone, collagen, heparinized collagen, tetrafluoroethylene, fluorinated polymer, fluorinated elastomer, flexible fused silica, polyolefin, polyester, polysilicon, stainless steel, Nitinol, titanium, a mixture of biocompatible materials, combinations thereof, and the like.

In yet another embodiment, a composite biocompatible material may be utilized by surface coating the above-mentioned biomaterial, wherein the coating material may be selected from the group consisting of polytetrafluoroethylene (PTFE), polyimide, hydrogel, heparin, therapeutic drugs, and the like.

In one embodiment, the material for the stent 31 (FIGS. 3-6) comprises one or more of a porous material, a semi-rigid material, a soft material, a hydrophilic material, a hydrophobic material, a hydrogel, an elastic material, or combinations thereof, and the like. The trabecular stent 31, particularly the porous stent, may have high water affinity that is hydrophilic and tissue compatible. One or more suitable drug may be coated or loaded onto the trabecular stent 31 and slowly released to the surrounding tissue which are effective to treat glaucoma and/or other ophthalmology abnormalities. As is well known in the art, a device coated or loaded with a slow-release drug can have prolonged effects on local tissue surrounding the device. The slow-release delivery can be designed such that an effective amount of drug is released over a desired duration.

In one embodiment, the stent device 31 (FIGS. 3-6) comprises a biodegradable (also including bioerodible) material admixed with a drug for drug slow-release into ocular tissues. In another embodiment, polymer films may function as drug containing release devices whereby the polymer films are coupled or secured to the device 31. The polymer films may be designed to permit the controlled release of the drug at a chosen rate and for a selected duration, which may also be episodic or periodic. Such polymer films may be synthesized such that the drug is bound to the surface or resides within a pore in the film so that the drug is relatively protected from enzymatic attack. The polymer films may also be modified to alter their hydrophilicity, hydrophobicity and vulnerability to platelet adhesion and enzymatic attack.

In some embodiments, the implant device 31 (FIGS. 3-6) is used for a direct release of pharmaceutical preparations into ocular tissues. As discussed above, pharmaceuticals may be compounded within the device 31 or form a coating on the device 31. Any known drug therapy for glaucoma and/or ophthalmology diseases may be utilized, including but limited to, the following:

U.S. Pat. No. 6,403,590, issued Jun. 11, 2002, the entire contents of which are hereby incorporated by reference herein, discloses isoquinolinesulfonyl compounds used in ophthalmic compositions to treat glaucoma or other ischemic-borne ocular disorders such as retinopathies or optic neuropathies. These compounds vasodilate ocular blood vessels, lower IOP and prevent or reduce the progression of visual field loss;

U.S. Pat. No. 6,274,138, issued Aug. 14, 2001 and U.S. Pat. No. 6,231,853, issued May 15, 2001, the entire contents of each one of which are hereby incorporated by reference herein, disclose the function of mitochondria and toxic drugs synthesized as a metabolic byproduct within mitochondria of cells. Perry and associates (Perry H D et al. "Topical cyclosporin A in the management of postkeratoplasty glaucoma" *Cornea* 16:284-288, 1997) report that topical cyclosporin-A has been shown to reduce post-surgical increase in intraocular pressure. It is proposed that such compounds with known effects on mitochondrial stability might be effective in treating trabecular meshwork. An antagonistic drug to neutralize the toxic byproduct or a stabilizing drug to effect mitochondrial stability is believed able to restore the mitochondria function and subsequently mitigate the dysfunction of the trabecular meshwork;

U.S. Pat. No. 6,201,001, issued Mar. 13, 2001, the entire contents of which are hereby incorporated by reference herein, discloses Imidazole antiproliferative agents useful for neovascular glaucoma;

U.S. Pat. No. 6,228,873, issued May 8, 2001, the entire contents of which are hereby incorporated by reference herein, discloses a new class of compounds that inhibit function of sodium chloride transport in the thick ascending limb of the loop of Henle, wherein the preferred compounds useful are furosemide, piretanide, benzmetanide, bumetanide, torasemide and derivatives thereof;

U.S. Pat. No. 6,194,415, issued Feb. 27, 2001, the entire contents of which are hereby incorporated by reference herein, discloses a method of using quinoxoalines (2-imidazolin-2-ylamino) in treating neural injuries (e.g. glaucomatous nerve damage);

U.S. Pat. No. 6,060,463, issued May 9, 2000 and U.S. Pat. No. 5,869,468, issued Feb. 9, 1999, the entire contents of each one of which are hereby incorporated by reference herein, disclose treatment of conditions of abnormally increased intraocular pressure by administration of phosphonylmethoxyalkyl nucleotide analogs and related nucleotide analogs;

U.S. Pat. No. 5,925,342, issued Jul. 20, 1999, the entire contents of which are hereby incorporated by reference herein, discloses a method for reducing intraocular pressure by administration of potassium channel blockers;

U.S. Pat. No. 5,814,620, issued Sep. 29, 1998, the entire contents which are hereby incorporated by reference herein, discloses a method of reducing neovascularization and of treating various disorders associated with neovascularization. These methods include administering to a tissue or subject a synthetic oligonucleotide;

U.S. Pat. No. 5,767,079, issued Jun. 16, 1998, the entire contents of which are hereby incorporated by reference herein, discloses a method for treatment of ophthalmic disorders by applying an effective amount of Transforming Growth Factor-Beta (TGF-beta) to the affected region;

U.S. Pat. No. 5,663,205, issued Sep. 2, 1997, the entire contents which are hereby incorporated by reference herein, discloses a pharmaceutical composition for use in glaucoma treatment which contains an active ingredient 5-[1-hydroxy-2-[2-(2-methoxyphenoxy)ethylamino]ethyl]-2-methylbenzenesulfonamide. This agent is free from side effects, and stable and has an excellent intraocular pressure reducing activity at its low concentrations, thus being useful as a pharmaceutical composition for use in glaucoma treatment;

U.S. Pat. No. 5,652,236, issued Jul. 29, 1997, the entire contents of which are hereby incorporated by reference herein, discloses pharmaceutical compositions and a method for treating glaucoma and/or ocular hypertension in the mammalian eye by administering thereto a pharmaceutical composition which contains as the active ingredient one or more compounds having guanylate cyclase inhibition activity. Examples of guanylate cyclase inhibitors utilized in the pharmaceutical composition and method of treatment are methylene blue, butylated hydroxyanisole and N-methylhydroxylamine;

U.S. Pat. No. 5,547,993, issued Aug. 20, 1996, the entire contents of which are hereby incorporated by reference herein, discloses that 2-(4-methylaminobutoxy) diphenylmethane or a hydrate or pharmaceutically acceptable salt thereof have been found useful for treating glaucoma;

U.S. Pat. No. 5,502,052, issued Mar. 26, 1996, the entire contents of which are hereby incorporated by reference herein, discloses use of a combination of apraclonidine and timolol to control intraocular pressure. The compositions contain a combination of an alpha-2 agonist (e.g., para-amino clonidine) and a beta blocker (e.g., betaxolo);

U.S. Pat. No. 6,184,250, issued Feb. 6, 2001, the entire contents of which are hereby incorporated by reference herein, discloses use of cloprostenol and fluprostenol analogues to treat glaucoma and ocular hypertension. The method comprises topically administering to an affected eye a composition comprising a therapeutically effective amount of a combination of a first compound selected from the group consisting of beta-blockers, carbonic anhydrase inhibitors, adrenergic agonists, and cholinergic agonists; together with a second compound;

U.S. Pat. No. 6,159,458, issued Dec. 12, 2000, the entire contents of which are hereby incorporated by reference herein, discloses an ophthalmic composition that provides sustained release of a water soluble medicament formed by comprising a crosslinked carboxy-containing polymer, a medicament, a sugar and water;

U.S. Pat. No. 6,110,912, issued Aug. 29, 2000, the entire contents of which are hereby incorporated by reference herein, discloses methods for the treatment of glaucoma by administering an ophthalmic preparation comprising an effective amount of a non-corneotoxic serine-threonine kinase inhibitor, thereby enhancing aqueous outflow in the eye and treatment of the glaucoma. In some embodiments, the method of administration is topical, whereas it is intracameral in other embodiments. In still further embodiments, the method of administration is intracanalicular;

U.S. Pat. No. 6,177,427, issued Jan. 23, 2001, the entire contents of which are hereby incorporated by reference herein, discloses compositions of non-steroidal glucocorticoid antagonists for treating glaucoma or ocular hypertension; and U.S. Pat. No. 5,952,378, issued Sep. 14, 1999, the entire contents of which are hereby incorporated by reference herein, discloses the use of prostaglandins for enhancing the delivery of drugs through the uveoscleral route to the optic nerve head for treatment of glaucoma or other diseases of the optic nerve as well as surrounding tissue. The method for enhancing the delivery to the optic nerve head comprises contacting a therapeutically effective amount of a composition containing one or more prostaglandins and one or more drug drugs with the eye at certain intervals.

Surgical Methods and Apparatus

FIGS. 7A-7D show one embodiment of an apparatus and illustrate steps of using it to create an opening in the trabecular meshwork and delivering a stent implant to a surgical site within the eye. FIG. 8 is another view of the apparatus highlighting certain features of the apparatus.

Figure 7A:
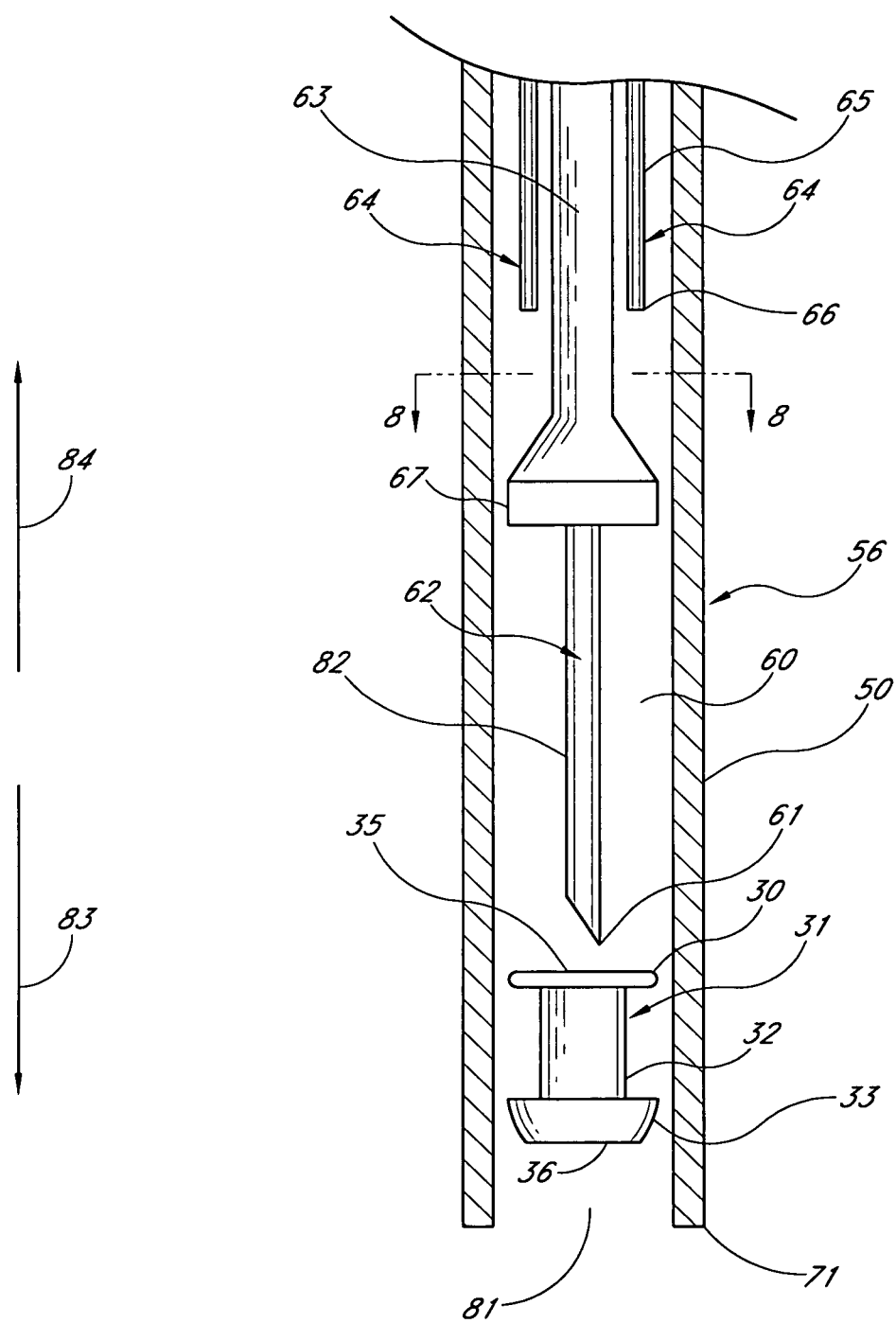
FIG. 7A is a partially cross-section view of an apparatus illustrating a first step of delivering the stent implant of FIG. 3 by holding the stent implant inside a lumen of an applicator and having features and advantages in accordance with one embodiment of the invention.
Figure 7B:
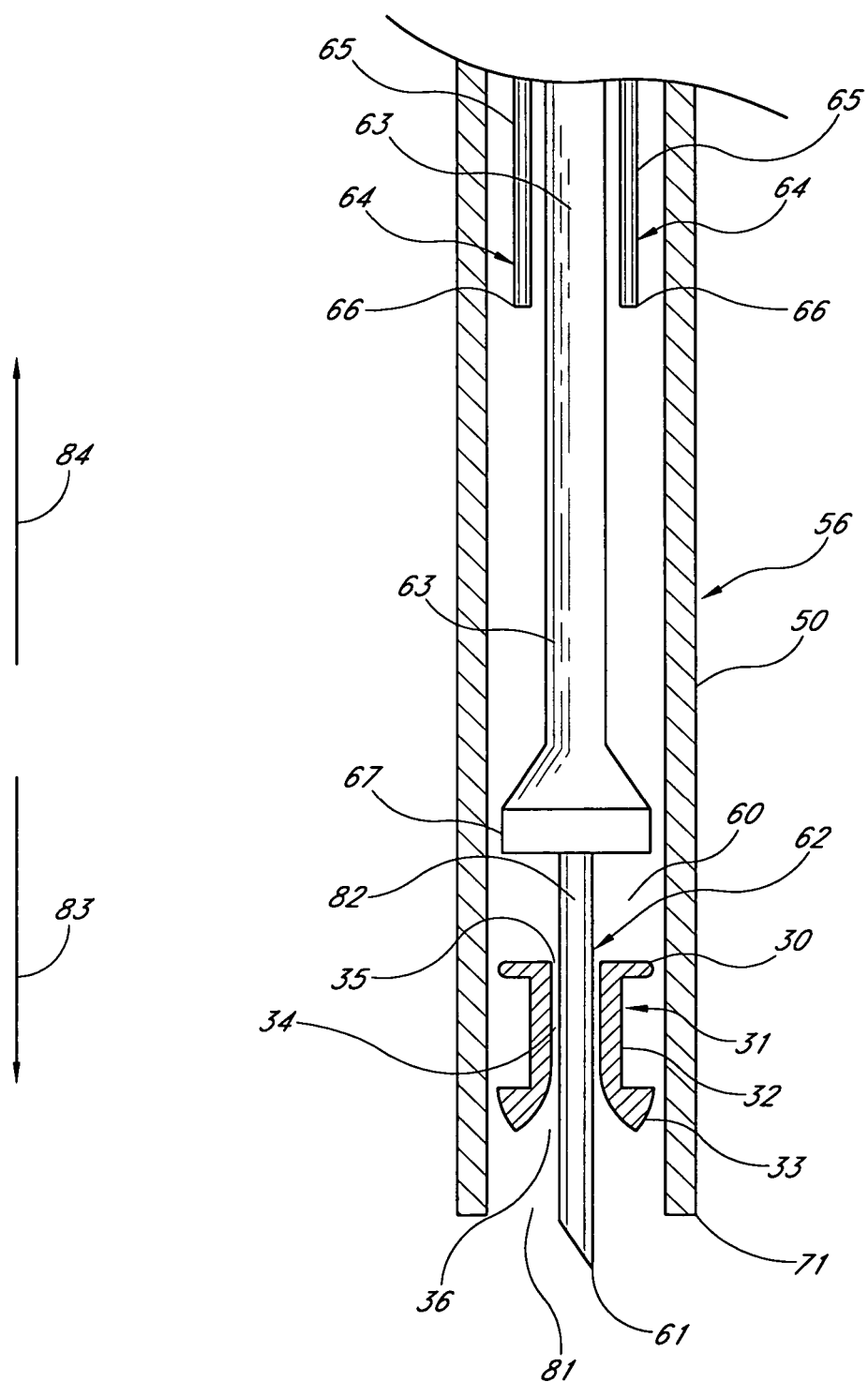
FIG. 7B is a partially cross-section view of the apparatus of FIG. 7A illustrating a second step of delivering the stent implant of FIG. 3 by creating an opening in the trabecular meshwork with a piercing member and having features and advantages in accordance with one embodiment of the invention.
Figure 7C:
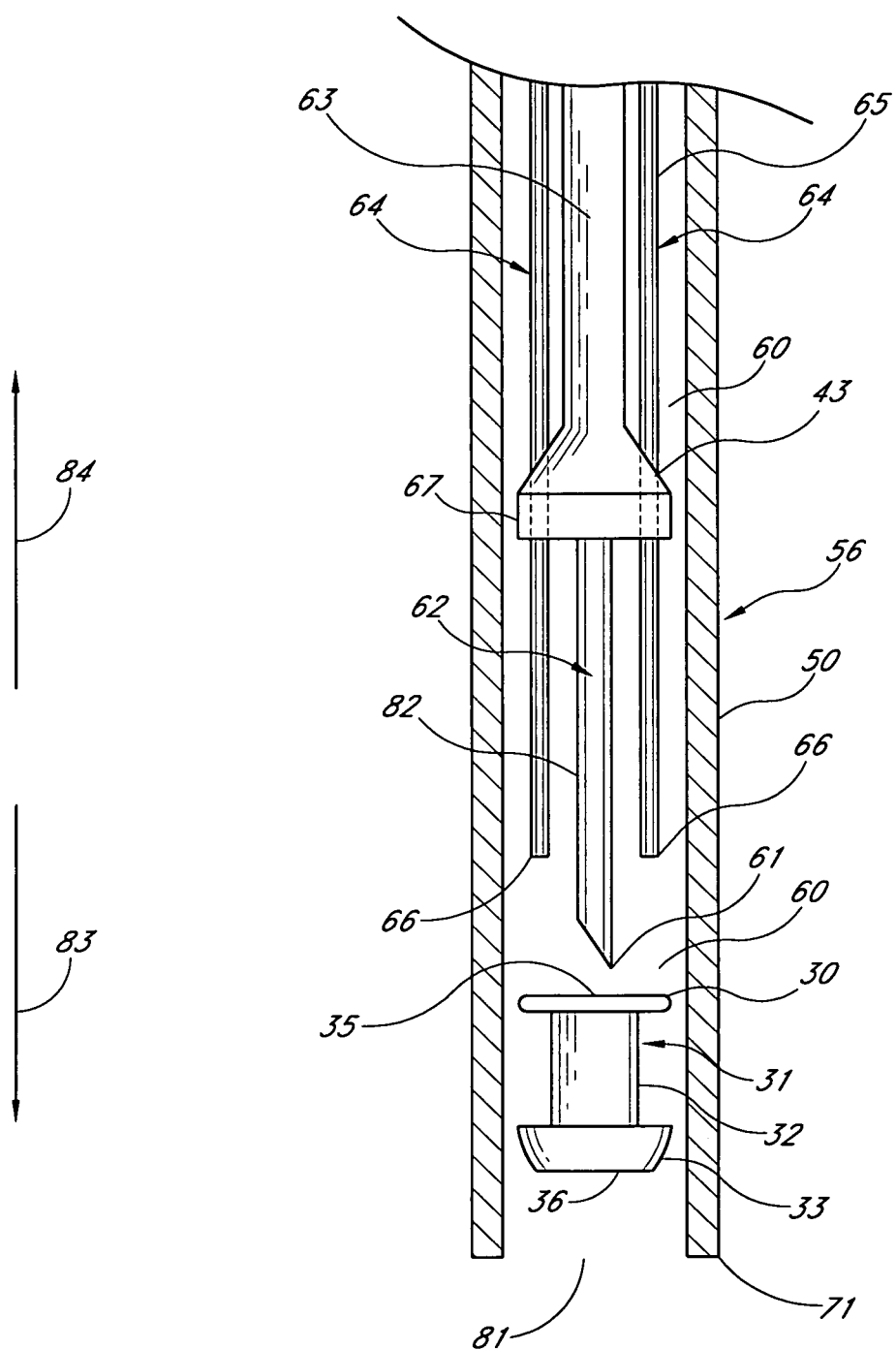
FIG. 7C is a partially cross-section view of the apparatus of FIG. 7A illustrating a third step of delivering the stent implant of FIG. 3 by retracting the piercing member inside the lumen of the applicator and having features and advantages in accordance with one embodiment of the invention.
Figure 7D:
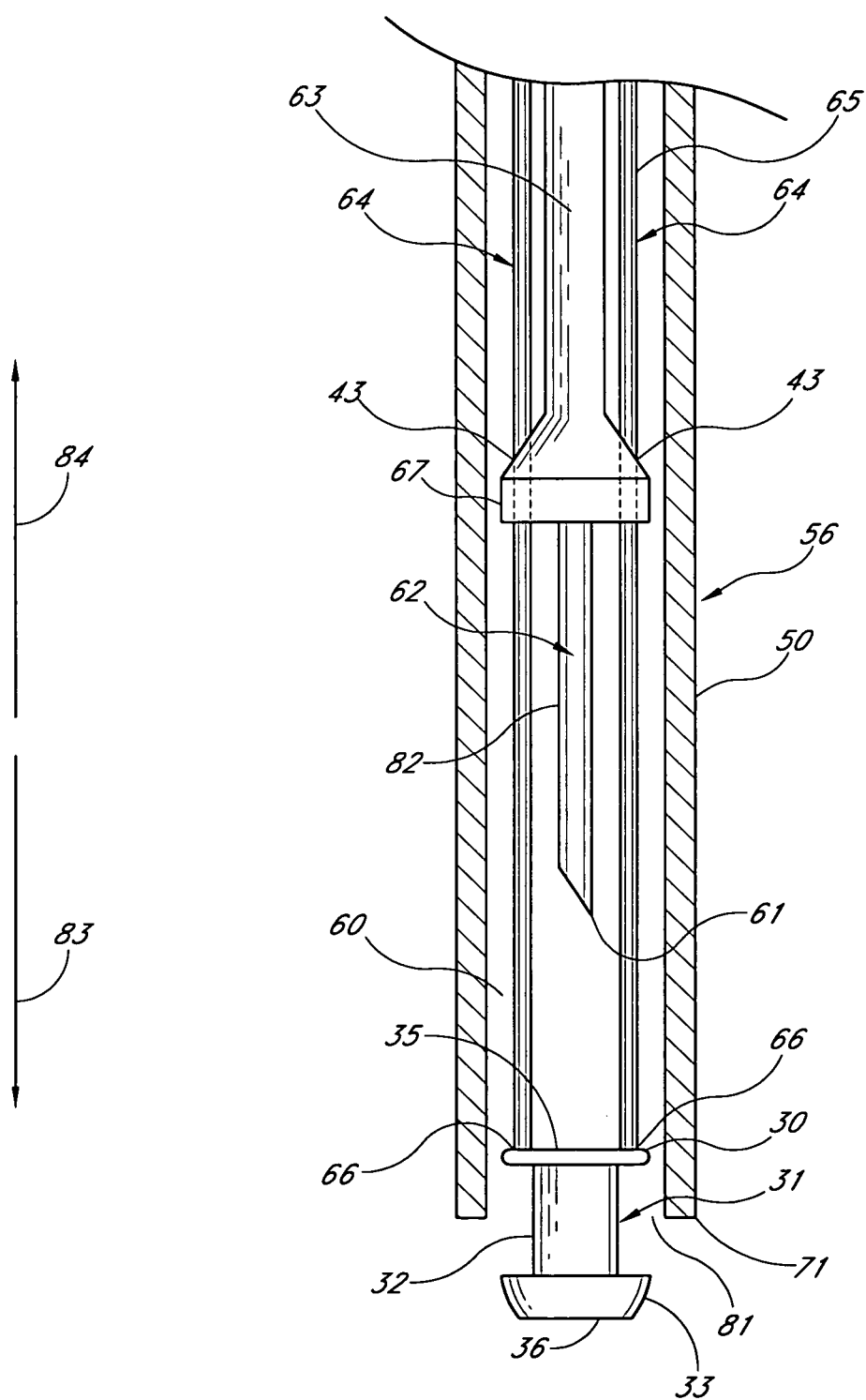
FIG. 7D is a is a partially cross-section view of the apparatus of FIG. 7A illustrating a fourth step of delivering the stent implant of FIG. 3 by inserting the stent implant through the trabecular meshwork and having features and advantages in accordance with one embodiment of the invention.
Figure 8:
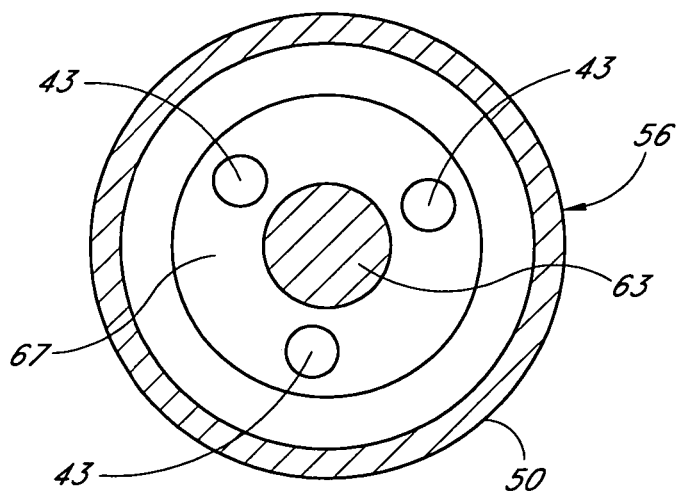
FIG. 8 is a cross-section view of the apparatus of FIGS. 7A-7D along line 8-8 of FIG. 7A.

Referring to the illustrated embodiment of FIGS. 7A-8, the apparatus or stent-delivery applicator 56 generally comprises a generally cylindrical outer housing, cover or sheath 50, a lumen or passage 60, a piercing member, device or mechanism 62 and a stent-delivery device or mechanism 64. The applicator or applicator portion 56 has an opening or orifice 81 at a distal-most end 71. The stent implant 31 or other suitable stent device is loaded within the applicator 56 at about the distal end or section 71 and resides within the applicator lumen 60.

In the illustrated embodiment of FIGS. 7A-8, the piercing member 62 generally comprises a distal section 82 having a distal end or piercing tip 61, a medial body portion or section 67 and a proximal deployment section or mechanism 63. As illustrated by the drawings, the piercing member 62 is moveably located or mounted within the lumen 60 of the applicator 56. The piercing member distal section 82, distal end 61 along with the body 67 can be moved forwardly (in the general direction of arrow 83) and backwardly (in the general direction of arrow 84) by the deployment mechanism 63 inside the lumen 60 of the applicator 56.

The piercing member distal end 61 (FIGS. 7A-7D) is sized and configured to effectively create an opening in the trabecular meshwork 21 enabling the stent 31 to be inserted with little resistance or effort and implanted (as shown, for example, in FIG. 6). In accordance with one aspect, the means or device for forming a hole, opening or incision in the trabecular mesh 21 may comprise a microknife, a pointed guidewire, a sharpened trephine, a screw shaped trephine, an irrigating tubing, a retinal pick, a microcurrette, or the like. In accordance with another aspect, the trabecular meshwork 21 may be pierced with an energy-assisted device, such as a laser optic fiber, a radiofrequency (RF) electrode, an ultrasonic transducer, a microwave antenna, a heated or cooled instrument or the like. Fiberoptic lasers that are suitable for such use include, for example, Q-switched Neodymiun (Nd):YAG lasers, Erbium:YAG lasers, cold $CO_2$ lasers and the like.

Figure 12:
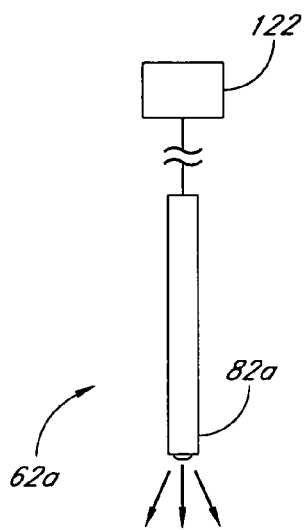
FIG. 12 is a simplified view of a piercing member comprising a laser probe having features and advantages in accordance with one embodiment of the invention.

FIG. 12 shows one embodiment of a piercing member 62a comprising a laser probe 82a. An energy source 122 is utilized to operate the laser probe 82a.

Figure 13:
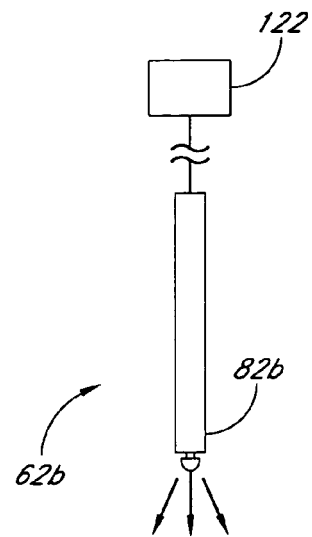
FIG. 13 is a simplified view of a piercing member comprising a radiofrequency transmitter having features and advantages in accordance with one embodiment of the invention.

FIG. 13 shows one embodiment of an energy-assisted piercing member 62b comprising a radiofrequency transmitter 82b. An energy source 122 is utilized to operate the radiofrequency transmitter 82b.

Figure 14:
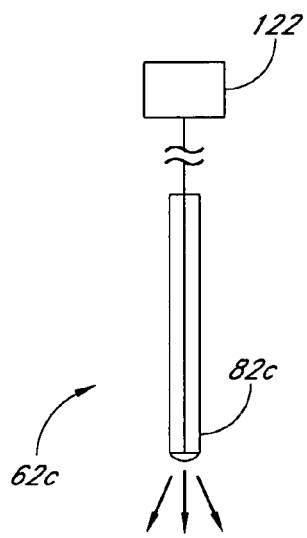
FIG. 14 is a simplified view of a piercing member comprising an optic fiber having features and advantages in accordance with one embodiment of the invention.

FIG. 14 shows one embodiment of an energy-assisted piercing member 62c comprising an optic fiber 82c. An energy source 122 is utilized to operate the optic fiber 82c.

Figure 15:
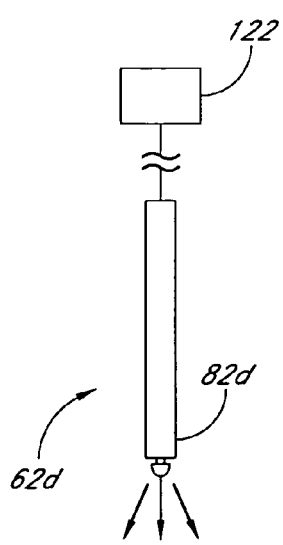
FIG. 15 is a simplified view of a piercing member comprising a microwave antenna having features and advantages in accordance with one embodiment of the invention.

FIG. 15 shows one embodiment of an energy-assisted piercing member 62d comprising a microwave antenna 82d. An energy source 122 is utilized to operate the microwave antenna 82d.

Figure 16:
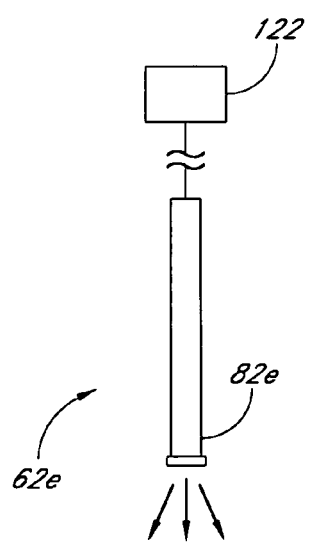
FIG. 16 is a simplified view of a piercing member comprising an ultrasound transducer having features and advantages in accordance with one embodiment of the invention.

FIG. 16 shows one embodiment of an energy-assisted piercing member 62e comprising an ultrasound transducer 82e. An energy source 122 is utilized to operate the ultrasound transducer 82e.

As best seen in FIG. 8, the piercing member body 67 includes a plurality of holes or openings 43. In the illustrated embodiment, the body portion 67 includes three holes 43 though fewer or more holes may be efficaciously utilized, as needed or desired. The holes 43 are sized and configured to provide passages for the stent-delivery mechanism 64 to engage and disengage from the stent 31 during implantation of the stent 31.

Figure 11:
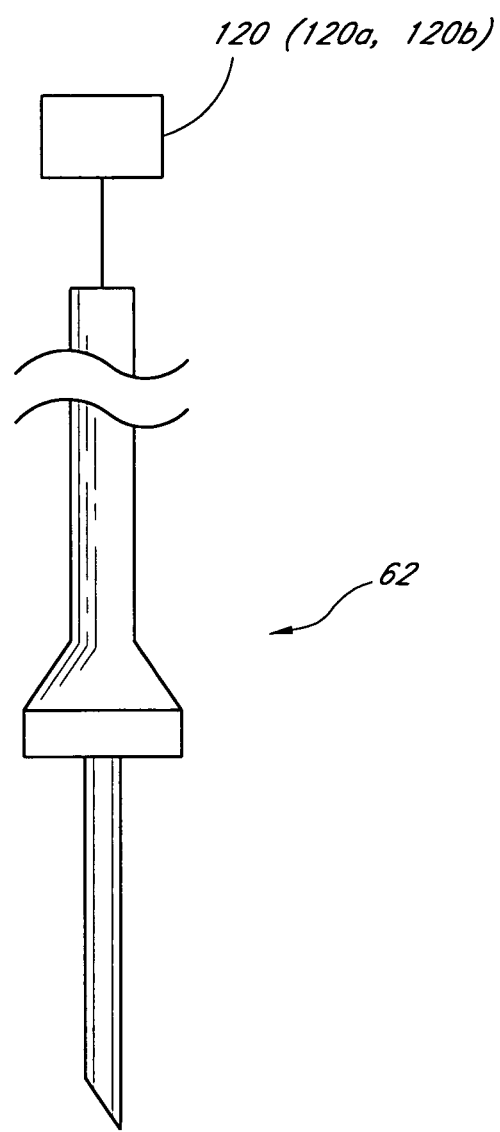
FIG. 11 is a simplified view of an applicator piercing member and a motion providing energy source or storage having features and advantages in accordance with embodiment of the invention.

In the illustrated embodiment of FIGS. 7A-8, the deployment mechanism 63 provides for the movement of the piercing member distal section 82 in the general directions 83 and 84. The deployment mechanism 63 may comprise any one of a number of suitable devices adapted to provide reciprocating motion. These may be manually or electronically actuated. For example, a spring-loaded plunger mechanism may be utilized to provide forward and backward motion to the piercing member distal section 82. Any one of a number or suitable actuators, for example, a solenoid actuator may be utilized to operate the deployment mechanism or device 63. FIG. 11 shows one schematic embodiment of an energy source or energy storage device 120 for providing reciprocating (advancing and retracting) motion to the piercing member 62. The source or storage device 120 can comprise an energy source such as a solenoid actuator 120*a* or a spring 120*b*.

In the illustrated embodiment of FIGS. 7A-7D, the stent-delivery mechanism 64 generally comprises a plurality of elongated rods, members or elements 65 with distal ends or sections 66. The stent-delivery mechanism 64 is moveably located or mounted within the lumen 60 of the applicator 56. The stent-delivery elements 65 can be moved forwardly (in the general direction of arrow 83) and backwardly (in the general direction of arrow 84) by a suitable deployment mechanism. The deployment mechanism may comprise any one of a number of suitable devices adapted to provide reciprocating motion. These may be manually or electronically actuated. For example, a spring-loaded plunger mechanism may be utilized to provide forward and backward motion to the stent-delivery elements 65. Any one of a number of suitable actuators, for example, a solenoid actuator may be utilized to operate the stent-delivery mechanism or device 64.

FIG. 7A illustrates a first step of delivering the stent implant 31 by holding the stent 31 inside the lumen 60 of the applicator or applicator portion 61. During the delivery stage, the applicator 56 as shown in FIG. 7A is introduced through a small incision on the cornea or sclera wall of the eye. The small incision may be less than about 1 mm in size and designated as "Sub one" incision. In one embodiment, the distal end 71 of the applicator 56 approaches the trabecular meshwork 21 on the opposite side of the small incision when a generally straight or slightly curved applicator is utilized (as discussed below in connection with FIG. 9). In another embodiment, the distal end 71 of the applicator 56 approaches the trabecular meshwork 21 on the same side of the small incision when a generally curved applicator is utilized.

FIG. 7B illustrates a second step of delivering the stent implant 31 by creating an opening in the trabecular meshwork 21 using the piercing member 62. (The piercing tip 61 or the piercing member 62 in general may comprise mechanical or energy-assisted piercing capabilities, as disclosed above.) The deployment mechanism 63 is actuated and the piercing member distal section 82 and piercing tip 61 are advanced in the forward direction 83. In the illustrated embodiment, the piercing member distal section 82 and piercing tip 61 travel through the stent lumen 34 and out of the lumen 60 through the lumen orifice 81 to engage the trabecular meshwork 21. The piercing step may comprise either partially piercing into the trabecular meshwork 21 or completely piercing through the trabecular meshwork 21 to facilitate the stent insertion in the trabecular bypass surgery disclosed herein. The length of the piercing member distal section 82 is sized for adequate piercing without causing damage or injury to the backside or rear of Schlemm's canal 22.

FIG. 7C illustrates a third step of delivering the stent implant 31 by retracting the piercing member distal section 82 into the lumen 60 of the applicator 56. The deployment mechanism 63 is actuated and the piercing member distal section 82 and piercing tip 61 are retracted in the backward direction 84. In the illustrated embodiment, the piercing member distal section 82 and piercing tip 61 travel the lumen orifice 81 and the stent lumen 34 and into the lumen 60. FIG. 7C also illustrates the actuation of the stent-delivery mechanism 64 and the advancement of the delivery elements 65 through the guidance or alignment holes 43 in the forward direction 83.

In some embodiments, the step of retracting the piercing member 62 (and piercing member distal section 82) as shown in FIG. 7C may be delayed or modified. This would allow guidance of the stent delivery so that the stent 31 may be advanced along and within the guiding environment of the piercing member 62 when the piercing member distal section 82 is still extended out of the distal point 71 of the applicator 56 and through the stent lumen 34. Thus, undesirable movement of the stent 31 is advantageously restricted or substantially eliminated.

FIG. 7D illustrates a fourth step of delivering the stent implant 31 by inserting the stent 31 through the opening (or partial or full incision) created in the trabecular meshwork 21 by the piercing member 62. In the illustrated embodiment, preferably immediately after retraction of the piercing member 62, the stent delivery mechanism 64 is activated by advancing the delivery elements 65 through the throughput holes 43 in the forward direction 83. The throughput holes 43 are used to guide the delivery elements 65 for effective stent delivery into the opening of the trabecular meshwork 21. The distal ends 66 contact or abut against the stent upper section 30 and guide the stent 31 into the opening (or incision) created in the trabecular meshwork 21. In the illustrated embodiment, the stent 31 travels out of the lumen 60 through the lumen orifice 81 to engage the trabecular meshwork 21. Once the stent has been implanted, the delivery elements 65 are retracted in the backward direction 84.

Some aspects of the invention provide an applicator for placing a trabecular stent into trabecular meshwork. The applicator generally comprises a sheath for holding the trabecular stent within a lumen of the sheath. The trabecular stent generally comprises an inlet section, an outlet section and a lumen extending from the inlet section to the outlet section. The applicator includes a piercing member located within the sheath, wherein the piercing member is slidably moveable through the lumen of the trabecular stent for creating an opening at about the trabecular meshwork. The applicator further includes a stent delivery mechanism for delivering the stent through the opening. The stent may further comprise a middle section between the inlet section and the outlet section, wherein the circumference of the middle section is smaller than the circumference of the inlet section.

Figure 9:
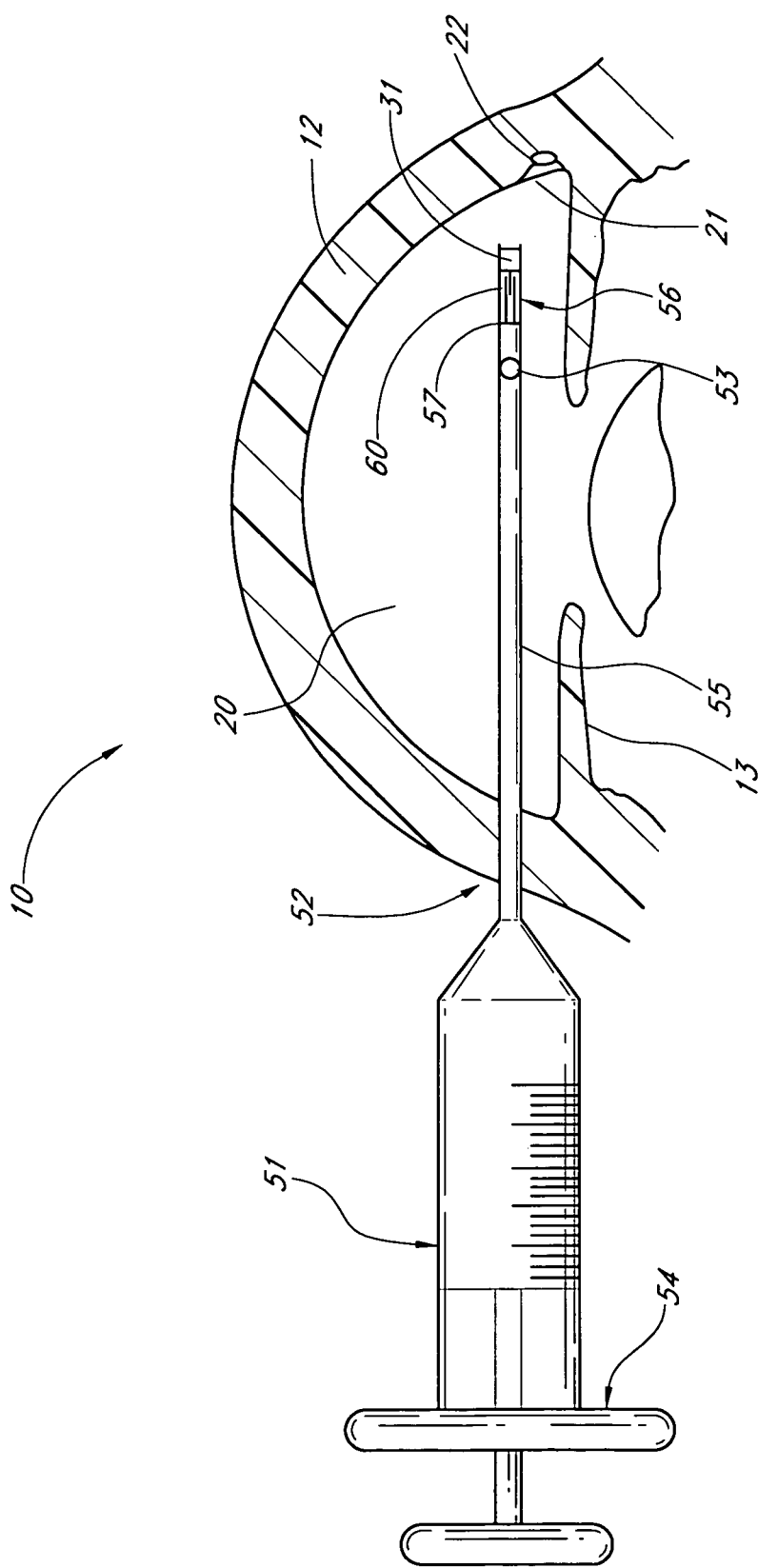
FIG. 9 illustrates one preferred exemplary method for placing the stent implant of FIG. 3 at the implant site having features and advantages in accordance with one embodiment of the invention.

FIG. 9 illustrates a method for placing the stent implant 31 or other suitable stent device at the implant site. In the illustrated embodiment, the stent-delivery applicator or applicator portion 56 is incorporated into an irrigating or irrigation apparatus or device 51. The apparatus 51 generally comprises a syringe portion 54 and a cannula portion 55 and/or the applicator portion 56. The distal section of the cannula portion 55 may have at lease one irrigating hole 53. The applicator 56 or the applicator portion is used to hold and implant the stent 31 using the piercing member 62 (including the deployment mechanism 63) and the stent delivery mechanism 64, as described above in connection with FIGS. 7A-7D. The proximal end 57 of the lumen 60 of the distal applicator portion 56 may be sealed from the remaining lumen of the cannula portion 55 to prevent fluid leakage.

In an exemplary embodiment of the trabecular meshwork surgery, the patient is placed in the supine position, prepped, draped and administered anesthesia. In one embodiment, a small (less than 1 mm in a "Sub one" surgery) self-sealing incision 52 (FIG. 9) is made in the cornea 12 opposite the stent placement site. The stent-loaded applicator 56 is advanced through the corneal incision 52 across the anterior chamber 20 held in the irrigating apparatus 51 under gonioscopic (lens) or endoscopic guidance, as illustrated in FIG. 9. The applicator 56 is used to make an incision in the trabecular meshwork 21 and implant the stent 31, as described in detail above, advantageously, in a one-step procedure. The irrigating apparatus 51 and the applicator 56 (without the stent) are withdrawn from the eye 10 and the surgery concluded.

Some aspects provide a method for inserting a trabecular stent through trabecular meshwork comprising: holding the trabecular stent within a lumen of an applicator, wherein the applicator comprises a slidably moveable piercing member located within the lumen of the applicator; delivering the applicator to about a surface of the trabecular meshwork; advancing the piercing member through a lumen of the trabecular stent for creating an opening at the trabecular meshwork; and inserting the trabecular stent into the opening. In one embodiment, the step of delivering the applicator is carried out by passing through a small incision at a cornea of an eye, wherein the small incision could be less than one millimeter in size.

Figure 17:
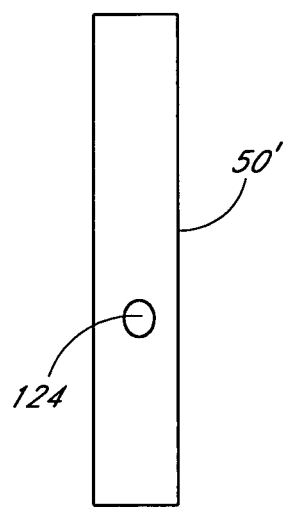
FIG. 17 is a simplified front view of an applicator outer housing comprising an opening configured to allow fluid infusion into the eye having features and advantages in accordance with one embodiment of the invention.

FIG. 17 shows one embodiment of an applicator outer housing 50'. The outer housing 50' comprises an opening 124 configured to allow fluid infusion into the eye.

Figure 18:
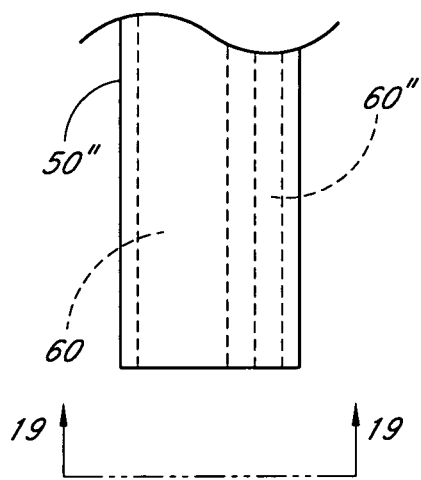
FIG. 18 is a simplified front view of an applicator housing comprising a fluid conducting lumen having features and advantages in accordance with one embodiment of the invention.
Figure 19:
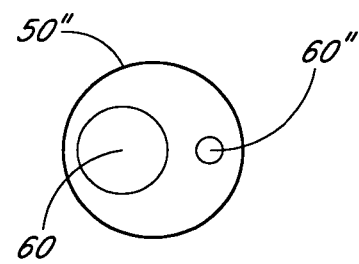
FIG. 19 is a distal end view of the housing of FIG. 18 along line 19-19 of FIG. 19.

FIGS. 18 and 19 show one embodiment of an applicator housing 50". The housing 50" comprises a lumen 60" that conducts fluid toward a distal end portion of an applicator such as the distal end portion 71 of the applicator 56.

Some aspects provide a device and a method for clearing the obstructed lumen of a trabecular stent in an ab interno procedure. After a stent has been implanted at about the trabecular meshwork with one opening of the device exposed to the anterior chamber and the other opening of the device exposed to Schlemm's canal, the lumen of the trabecular stent may be obstructed, plugged or partially blocked with diminished aqueous transportation ability.

Figure 10:
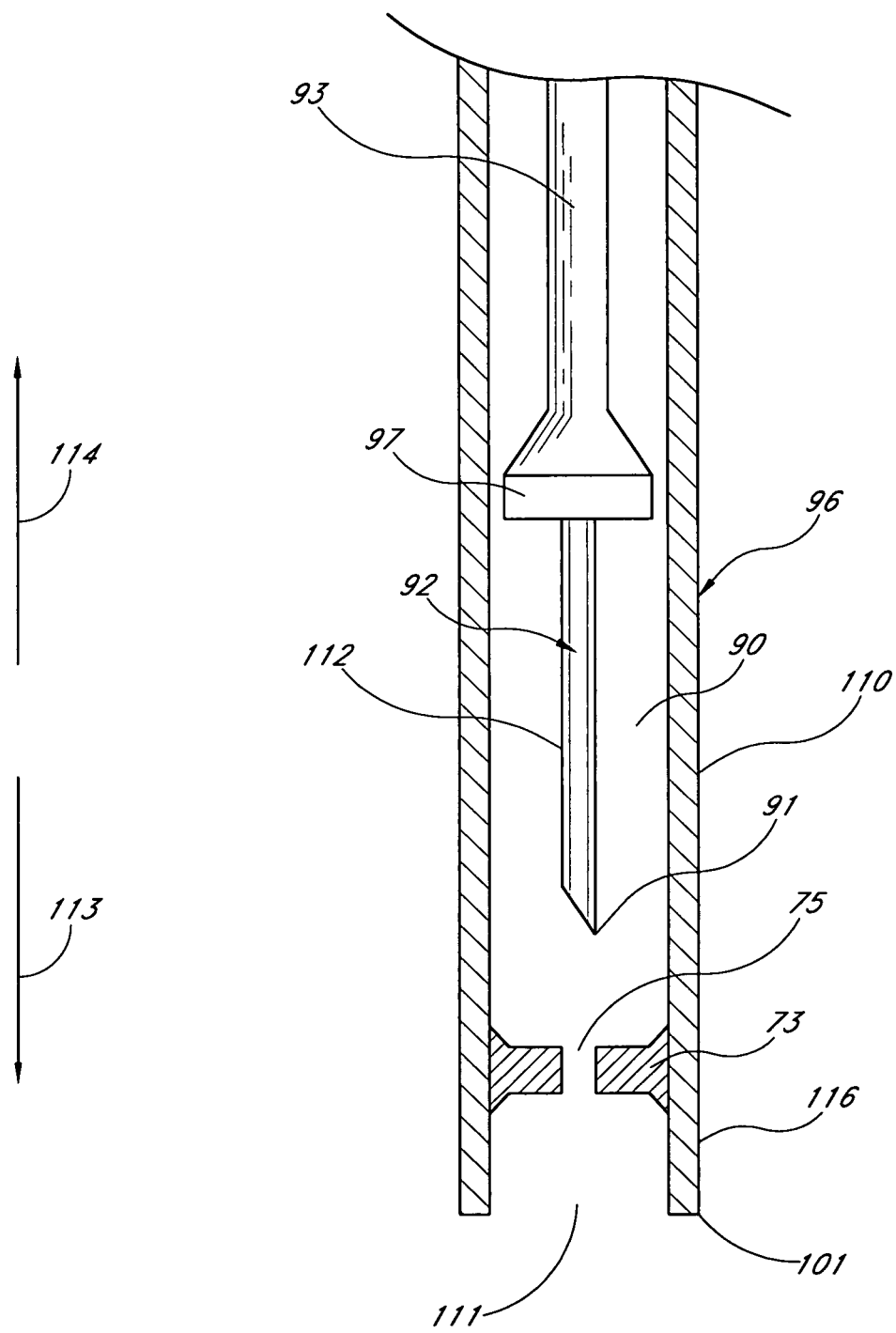
FIG. 10 is a partially cross-section view of an apparatus for clearing an obstructed lumen of the implanted trabecular stent of FIG. 3 having features and advantages in accordance with one embodiment of the invention.

A repairing applicator 96 as shown in FIG. 10 may be used to restore the aqueous transmission function through the implanted trabecular stent 31 or other plugged stent. The repairing applicator 96 generally comprises a generally cylindrical outer housing, cover or sheath 110, a lumen or passage 90, a piercing member, device or mechanism 92. The applicator or applicator portion 96 has an opening or orifice 111 at a distal-most end 101.

In the illustrated embodiment of FIG. 10, the piercing member 92 is axially moveable within the lumen 90 of the applicator 96. The piercing member 92 generally comprises a distal section 112 having a distal end or piercing tip 91, a medial body portion or section 97 and a proximal deployment section or mechanism 93. The piercing member 92 is moveably located or mounted within the lumen 90 of the applicator 96. The piercing member distal section 112, distal end 91 along with the body 97 can be moved forwardly (in the general direction of arrow 113) and backwardly (in the general direction of arrow 114) by the deployment mechanism 93 inside the lumen 90 of the applicator 96.

The piercing member distal end 91 (FIG. 10) is sized and configured to effectively clear any obstruction inside the opening or lumen of an implanted stent. To help guide and support the piercing member 92, a supporter or support element 73 with a concentric hole 75 at its center sized for allowing the piercing member distal section 112 and distal end 91 to easily pass through is secured at a proper luminal location of a distal section 116 of the repairing applicator 96.

In accordance with one aspect, the means or device for clearing the obstruction inside the opening or lumen of an implanted stent may comprise a microknife, a pointed guidewire, a sharpened trephine, a screw shaped trephine, an irrigating tubing, a retinal pick, a microcurrette, or the like. In accordance with another aspect, the obstruction may be cleared with an energy-assisted device, such as a laser optic fiber, a radiofrequency (RF) electrode, an ultrasonic transducer, a microwave antenna, a heated or cooled instrument or the like. Fiberoptic lasers that are suitable for such use include, for example, Q-switched Neodymiun (Nd):YAG lasers, Erbium:YAG lasers, cold $CO_2$ lasers and the like.

In the illustrated embodiment of FIG. 10, the deployment mechanism 93 providers for the movement of the piercing member distal section 112 in the general directions 113 and 114. The deployment mechanism 93 may comprise any one of a number of suitable devices adapted to provide reciprocating motion. These may be manually or electronically actuated. For example, a spring-loaded plunger mechanism may be utilized to provide forward and backward motion to the piercing member distal section 112. Any one of a number of suitable actuators, for example, a solenoid actuator may be utilized to operate the deployment mechanism or device 93.

Some aspects provide a repairing applicator for clearing an obstructed lumen of an implanted trabecular stent. The repairing applicator generally comprises a sheath and a piercing member located within the sheath, wherein the piercing member is slidably moveable approaching the obstructed lumen of the implanted trabecular stent configured for clearing the lumen.

From the foregoing description, it will be appreciated that a novel approach for the surgical treatment of glaucoma has been disclosed for releasing excessive intraocular pressure. While the components, techniques and aspects of the invention have been described with a certain degree of particularity, it is manifest that many changes may be made in the specific designs, constructions and methodology herein above described without departing from the spirit and scope of this disclosure.

Various modifications and applications of the invention may occur to those who are skilled in the art, without departing from the true spirit or scope of the invention. It should be understood that the invention is not limited to the embodiments set forth herein for purposes of exemplification, but is to be defined only by a fair reading of the appended claims, including the full range of equivalency to which each element thereof is entitled.

What is claimed is:

1. A method for implanting an implant in an eye, the method comprising:
    providing a delivery device comprising a trocar and an implant mounted on the trocar;
    placing a distal end of the trocar against eye tissue;
    piercing the eye tissue with the distal end of the trocar;
    actuating a source of energy to expel the implant from a distal end of the delivery device and into the eye tissue such that at least a portion of the implant is placed into the eye tissue; and
    anchoring the implant in the eye tissue.

2. The method of claim 1, wherein the method further comprises eluting a drug from the implant.

3. The method of claim 1, wherein actuating a source of energy involves utilizing energy stored in the delivery device to expel the implant.

4. The method of claim 3, wherein utilizing energy stored in the delivery device involves utilizing electromagnetic energy or stored mechanical energy to expel the implant.

5. The method of claim 3, wherein utilizing energy stored in the delivery device involves utilizing at least one of a spring that stores mechanical energy and a solenoid actuator to expel the implant.

6. The method of claim 1, wherein the method further comprises inserting the distal end of the delivery device into an anterior chamber of the eye through a corneal incision.

7. The method of claim 6, wherein the method further comprises advancing the distal end of the delivery device through the anterior chamber to the eye tissue.

8. The method of claim 7, wherein the method further comprises advancing the distal end of the delivery device across the anterior chamber to the eye tissue.

9. The method of claim 1, wherein placing a distal end of a delivery device against eye tissue involves placing the distal end against a trabecular meshwork of the eye.

10. The method of claim 1, wherein placing a distal end of a delivery device against eye tissue involves placing the distal end against tissue that is a site of outflow of aqueous humor.

11. The method of claim 1, wherein placing a distal end of a delivery device against eye tissue involves placing the distal end proximate to a physiologic outflow pathway of the eye.

12. The method of claim 1, wherein the method further comprises placing at least a portion of the implant in a physiologic outflow path of the eye.

13. The method of claim 12, wherein placing at least a portion of the implant in a physiologic outflow path involves placing said at least portion of the implant in the physiologic path which comprises Schlemm's canal of the eye.

14. The method of claim 1, wherein the method further comprises placing at least a portion of the implant in a sclera of the eye.

15. The method of claim 1, wherein the method further comprises placing at least a portion of the implant in an anterior chamber of the eye.

16. The method of claim 1, wherein placement of said at least portion of the implant in eye tissue involves placing said at least portion in a trabecular meshwork of the eye.

17. The method of claim 1, wherein the eye tissue comprises at least one of a trabecular meshwork, a sclera, and a site of outflow of aqueous humor of the eye.

18. The method of claim 1, wherein anchoring the implant involves abutting a surface of the implant against the eye tissue to stabilize the implanted implant.

* * * * *